US005851774A

United States Patent [19]
Hillman et al.

[11] Patent Number: 5,851,774
[45] Date of Patent: Dec. 22, 1998

[54] HUMAN MLF3 PROTEIN

[75] Inventors: Jennifer L. Hillman, Mountain View; Surya K. Goli, Sunnyvale, both of Calif.

[73] Assignee: Incyte Pharmaceuticals, Inc., Palo Alto, Calif.

[21] Appl. No.: 805,965

[22] Filed: Feb. 25, 1997

[51] Int. Cl.$^6$ .............................. C12Q 1/68; C07H 21/00; C07H 21/02; C07H 21/04

[52] U.S. Cl. ........................... 435/6; 536/23.1; 536/23.5; 530/350; 530/380; 514/44; 435/69.1; 435/69.3; 435/320.1; 435/252.3

[58] Field of Search ................................ 514/44; 436/518; 435/5, 6, 69.1, 69.3, 71.1, 320.1, 243, 252.3; 536/23.1, 23.5; 530/350, 380; 935/22, 66–75

[56] References Cited

PUBLICATIONS

Kuefer et al., Gemonics vol. 35 p. 392, Jul. 1996.

Yoneda–Kato, N et al., "The t(3;5) (q25.1;134) of myelodysplastic syndrome and acute myeloid leukemia produces a novel fusion gene, NPM–MLF1" *Oncogene* 12(2):265–275 (1996) (GI 1066392 and GI 1066391).

Kuefer, MU et al., "cDNA cloning, tissue distribution, and chromosomal localization of myelodysplasia/myeloid leukemia factor 2 (MLF2)" *Genomics* 35(2):392–396 (1996) (GI 1399745 and GI 1399744).

Schimmel, P., "Aminoacyl tRNA synthetases: general scheme of structure–function relationships in the polypeptides and recognition of transfer RNAs" *Annu Rev Biochem* 56:125–158 (1987).

Brenner, S., "The molecular evolution of genes and proteins: a tale of two serines" *Nature* 334 (6182):528–530 (1988).

Garber, GE et al., "A Trichomonas vaginalis cDNA with partial protein sequence homology with a Plasmodium falciparum excreted protein ABRA" *Appl Parasitol* 34(4):245–249 (1993).

Yoneda–Kato, N. et al., (Direct Submission), GenBank Sequence Database (Accession 1066392), National Center for Biotechnology Information, National Library of Medicine, Bethesda, Maryland, 20894 (GI 1066392) (1996).

Yoneda–Kato, N. et al., (Direct Submission), GenBank Sequence Database (Accession L49054), National Center for Biotechnology Information, National Library of Medicine, Bethesda, Maryland, 20894 (GI 1066391) (1996).

Kuefer, M.U. et al., (Direct Submission), GenBank Sequence Database (Accession 1399745), National Center for Biotechnology Information, National Library of Medicine, Bethesda, Maryland, 20894 (GI 1399745) (1996).

Kuefer, M.U. et al., (Direct Submission), GenBank Sequence Database (Accession U57342), National Center for Biotechnology Information, National Library of Medicine, Bethesda, Maryland, 20894 (GI 1399744) (1996).

*Primary Examiner*—Sheela Huff
*Attorney, Agent, or Firm*—Lucy J. Billings; Incyte Pharmaceuticals, Inc.

[57] ABSTRACT

The present invention provides a novel human integral membrane (MLF3) and polynucleotides which identify and encode MLF3. The invention also provides genetically engineered expression vectors and host cells comprising the nucleic acid sequences encoding MLF3 and a method for producing MLF3. The invention also provides for agonists, antibodies, or antagonists specifically binding MLF3, and their use, in the prevention and treatment of diseases associated with expression of MLF3. Additionally, the invention provides for the use of antisense molecules to polynucleotides encoding MLF3 for the treatment of diseases associated with the expression of MLF3. The invention also provides diagnostic assays which utilize the polynucleotide, or fragments or the complement thereof, and antibodies specifically binding MLF3.

9 Claims, 11 Drawing Sheets

|     | 9   |     | 18  |     | 27  |     | 36  |     | 45  |     | 54  |     |
| --- | --- | --- | --- | --- | --- | --- | --- | --- | --- | --- | --- | --- |
| NGG | GGG | GCG | TAC | GGA | GGT | GGC | AGC | TGT | GGG | AGG | CGG | CGT | GGA | AGG | CCG | AGG | 108 |

|     | 63  |     | 72  |     | 81  |     | 90  |     | 99  |     | 108 |
| AGC | TCA | AGC | CCG | GAC | CAA | TCC | CGT | TCC | CCA | CCC | TGA | CCC | TGC | AGC | 162 |

|     | 117 |     | 126 |     | 135 |     | 144 |     | 153 |     |     |
| GTA | CCG | GGA | AGC | GAA | ACC | GGC | ATG | GGC | CGG | CCG | TGA | GCC | CGA | CAC | TGT | 216 |

|     | 171 |     | 180 |     | 189 |     | 198 |     | 207 |     |     |
| GTG | GAG | CCC | CCT | GGA | GCT | GAG | ATC | AGG | ATG | TTC | CGC | TTC | ATG | AGG | GAC | GTG | GAG | 270 |
|     |     |     |     |     |     |     |     |     | M   | F   | R   | F   | M   | R   | D   | V   | E   |

|     | 225 |     | 234 |     | 243 |     | 252 |     | 261 |     |     |
| CCT | GAG | GAT | CCC | ATG | TTC | CTG | ATG | GAT | CCC | TTT | GCT | ATT | CAC | CGT | CAG | CAT | ATG | 324 |
| P   | E   | D   | P   | M   | F   | L   | M   | D   | P   | F   | A   | I   | H   | R   | Q   | H   | M   |

|     | 279 |     | 288 |     | 297 |     | 306 |     | 315 |     |     |
| AGC | CGT | ATG | TTG | TCA | GGT | GGT | TTT | GGA | TAT | AGC | CCC | TTC | CTC | AGC | ATC | ACA | GAT | 378 |
| S   | R   | M   | L   | S   | G   | G   | F   | G   | Y   | S   | P   | F   | L   | S   | I   | T   | D   |

|     | 333 |     | 342 |     | 351 |     | 360 |     | 369 |     |     |
| GGC | AAC | CCA | GGG | ACC | AGG | GCT | GCC | AGC | CGG | ATG | CAG | GCT | GGA | GCT | 432 |
| G   | N   | P   | G   | T   | R   | A   | A   | S   | R   | M   | Q   | A   | G   | A   |

|     | 387 |     | 396 |     | 405 |     | 414 |     | 423 |     |     |
| GTC | TNC | CCC | TTT | GGG | NTG | CTG | GGA | ATG | TCG | GGT | TTC | ATG | GAC | ATG | TTT | GGG | 432 |
| V   | X   | P   | F   | G   | X   | L   | G   | M   | S   | G   | F   | M   | D   | M   | F   | G   |

FIGURE 1A

```
441              450              459              468              477              486
ATG ATG AAT      GAC ATG NTT      GGA AAC CAC      ATG GAA CAC      ACA GCT GGA      GGC AAT TGC
 M   M   N        D   M   X        G   N   H        M   E   H        T   A   G        G   N   C 495              504              513              522              531              540
CAG ACC TTC      TCA TCT ACT      GTC ATC TCC      TAC AAT ACG      GGT GAT GGT      GCC
 Q   T   F        S   S   T        V   I   S        Y   N   T        G   D   G        A 549              558              567              576              585              594
CCC AAG GTC      TAC CAA ACA      GAG TCA GAG      ATG CGC TCG      GCA CCA GGG      ATC CGG
 P   K   V        Y   Q   T        E   S   E        M   R   S        A   P   G        I   R 603              612              621              630              639              648
GAG ACA CGG      AGG ACT GTT      CGG GAT AGT      TCA GAC AGT      GGA CTG GAG      CAG ATG TCC ATT
 E   T   R        R   T   V        R   D   S        S   D   S        G   L   E        Q   M   S   I 657              666              675              684              693              702
GGG CAT CAC      ATC CGG AGG      GCT CAG CAG      CGC TCC CAG      CGC TCC CGA      AAC CAT CGC
 G   H   H        I   R   R        A   Q   Q        R   S   Q        R   S   R        N   H   R 711              720              729              738              747              756
ACG GGG GAC      CAG GAG GAG      CGG CAG GAG      CGG GAG ACC      AAC CTG GAT      GAG AGT GAG GCC
 T   G   D        Q   E   E        R   Q   E        R   E   T        N   L   D        E   S   E   A 765              774              783              792              801              810
GCA GCG TTT      GAT GAC GAG      TGG CGG GAG      ACC TCC CGA      TTC GAG AGT      CAG CAG CGT
 A   A   F        D   D   E        W   R   E        T   S   R        F   E   S        Q   Q   R
```

FIGURE 1B

```
CCC CTG GAG TTT CGG CTT GAG TCC TCA GGG GCT GGG GGA CGA AGG GCG GAG
 P   L   E   F   R   L   E   S   S   G   A   G   G   R   R   A   E
819     828     837     846     855     864

GGG CCT CCC CGC CTG GCC ATC CAG GGA CCT GAG TCC CTT CCC GAC AGT CCC
 G   P   P   R   L   A   I   Q   G   P   E   S   L   P   D   S   P
873     882     891     900     909     918

GCC GCT ATG ACT GGT GAG GGC CCC GGG GCC TCA GCT CTC TTG TAC AGG CTG AGA
 A   A   M   T   G   E   G   P   G   A   S   A   L   L   Y   R   L   R
927     936     945     954     963     972

GGC TGA GAA ATC ATC CCC TGA ATA ACT TTT TCC TCT CGA TTC TCC CCA ATT
 G   *   E   I   I   P   *   I   T   F   S   S   R   F   P   S   P   I
981     990     999     1008    1017    1026

TAA TAT TAA ATT AAC AGG CAA AGC CGG CCC CTA CCT TTT CCT CTG GGG GTC TCA GGG
 *   Y   *   I   N   R   Q   S   R   P   L   P   F   P   S   L   G   V   S   G
1035    1044    1053    1062    1071    1080

AGA ACC TTT CAC GGC ACC CTT TCC TTT CCT TCT TTA ATC TCC TGG TTT
 R   T   F   H   G   T   L   S   F   P   S   L   I   S   W   F
1089    1098    1107    1116    1125    1134

ACC ATT GAT GAC TTC GGC TCT GCA TCT ACT TAC TTG ATT TTT CAT TCT GCC ACT
 T   I   D   D   F   G   S   A   S   T   Y   L   I   F   H   S   A   T
1143    1152    1161    1170    1179    1188
```

FIGURE 1C

```
       1197          1206          1215          1224          1233          1242
TCA TCT TCA AAC CCC CTC ACC TTT CCC ATC CTA CTC CTG CCA TGC ATT GAA GGG
 S   S   S   N   P   L   T   F   P   I   L   L   L   P   C   I   E   G 1251          1260          1269          1278          1287          1296
TCA ATG CAT TTT GGG GTG AGN TTN GGT TTA GGG GCC CCT TCA TNC CTN AGC TAC
 S   M   H   F   G   V   X   X   G   L   G   A   P   S   X   L   S   Y 1305          1314          1323
CTG GGT CTT TGC CCA ACT TTT CTC AGA
 L   G   L   C   P   T   F   L   R
```

FIGURE 1D

|     |     |     |     |     |     |     |     |     |     |     |     |     |     |     |     |     |     |     |     |     |     |     |     |     |     |     |     |     |     |
| --- | --- | --- | --- | --- | --- | --- | --- | --- | --- | --- | --- | --- | --- | --- | --- | --- | --- | --- | --- | --- | --- | --- | --- | --- | --- | --- | --- | --- | --- |
| 1   | M   | F   | R   | F   | M   | R   | D   | V   | E   | P   | E   | D   | P   | M   | F   | L   | M   | D   | P   | F   | A   | I   | H   | R   | Q   | H   | M   | S   | R   | M   | 762280      |
| 1   | M   | F   | R   | M   | L   | N   | S   | S   | F   | E   | D   | D   | P   | -   | F   | F   | S   | E   | S   | I   | L   | A   | H   | R   | E   | N   | M   | R   | Q   | M   | GI 1066392  |
| 1   | M   | F   | R   | F   | M   | R   | D   | V   | E   | P   | E   | D   | P   | M   | F   | L   | M   | D   | P   | F   | A   | I   | H   | R   | Q   | H   | M   | S   | R   | M   | GI 1399745  |
| 31  | L   | -   | -   | -   | S   | G   | G   | F   | G   | Y   | S   | P   | F   | L   | S   | I   | T   | D   | G   | N   | M   | P   | G   | T   | R   | A   | A   | S   | R   | R   | 762280      |
| 30  | I   | R   | S   | F   | S   | E   | P   | F   | G   | -   | R   | D   | L   | L   | S   | I   | S   | D   | D   | G   | R   | -   | -   | G   | R   | A   | H   | N   | R   | R   | GI 1066392  |
| 31  | L   | -   | -   | -   | S   | G   | G   | F   | G   | Y   | S   | P   | F   | L   | S   | I   | T   | D   | G   | N   | M   | P   | G   | T   | R   | P   | A   | S   | R   | R   | GI 1399745  |
| 58  | M   | Q   | Q   | A   | G   | A   | -   | -   | -   | -   | -   | -   | V   | X   | P   | F   | G   | X   | L   | G   | M   | S   | G   | G   | F   | M   | D   | M   | F   | 762280      |
| 56  | G   | H   | N   | D   | G   | E   | D   | S   | L   | T   | H   | T   | D   | V   | S   | S   | F   | Q   | T   | M   | D   | Q   | M   | V   | S   | N   | M   | R   | N   | Y   | GI 1066392  |
| 58  | M   | Q   | Q   | A   | G   | A   | -   | -   | -   | -   | -   | -   | V   | S   | P   | F   | G   | M   | L   | G   | M   | S   | G   | G   | F   | M   | D   | M   | F   | GI 1399745  |
| 81  | G   | M   | M   | N   | D   | M   | X   | G   | N   | M   | E   | H   | M   | T   | A   | G   | G   | N   | C   | Q   | T   | F   | S   | S   | S   | T   | V   | I   | S   | Y   | 762280      |
| 86  | -   | -   | M   | Q   | K   | L   | E   | R   | N   | F   | G   | Q   | L   | S   | V   | D   | P   | N   | G   | H   | S   | F   | C   | S   | S   | S   | V   | M   | T   | Y   | GI 1066392  |
| 81  | G   | M   | M   | N   | D   | M   | I   | G   | N   | M   | E   | H   | M   | T   | A   | G   | G   | N   | C   | Q   | T   | F   | S   | S   | S   | T   | V   | I   | S   | Y   | GI 1399745  |
| 111 | S   | N   | T   | G   | D   | G   | A   | P   | K   | V   | Y   | Q   | E   | T   | S   | E   | M   | R   | S   | A   | P   | G   | G   | I   | R   | E   | T   | R   | R   | T   | 762280      |
| 114 | S   | K   | I   | G   | D   | E   | P   | P   | K   | V   | F   | Q   | A   | S   | T   | Q   | T   | R   | R   | A   | P   | G   | G   | I   | K   | E   | T   | R   | K   | A   | GI 1066392  |
| 111 | S   | N   | T   | G   | D   | G   | A   | P   | K   | V   | Y   | Q   | E   | T   | S   | E   | M   | R   | S   | A   | P   | G   | G   | I   | R   | E   | T   | R   | R   | T   | GI 1399745  |
| 141 | V   | R   | D   | S   | D   | S   | G   | L   | E   | Q   | M   | S   | I   | G   | H   | H   | I   | R   | D   | R   | A   | H   | I   | L   | Q   | R   | S   | R   | N   | H   | 762280      |
| 144 | M   | R   | D   | S   | D   | S   | G   | L   | E   | K   | M   | A   | I   | G   | H   | H   | I   | H   | D   | R   | A   | H   | V   | I   | K   | K   | S   | K   | N   | K   | GI 1066392  |
| 141 | V   | R   | D   | S   | D   | S   | G   | L   | E   | Q   | M   | S   | I   | G   | H   | H   | I   | R   | D   | R   | A   | H   | I   | L   | Q   | R   | S   | R   | N   | H   | GI 1399745  |

| Library | Lib Description | Abun | Pct Abun |
|---|---|---|---|
| BRAINOT11 | brain, right temporal, epilepsy, 5 M | 4 | 0.1289 |
| PITUNOT03 | pituitary, 46 M | 3 | 0.1045 |
| BRAINOM02 | brain, 55 M, NORM, WM | 2 | 0.0907 |
| PGANNOT03 | paraganglionic tumor, 46 M | 2 | 0.0622 |
| STOMNOT02 | stomach, 52 M, match to STOMTUT01 | 2 | 0.0615 |
| BRAINOT12 | brain, right frontal, epilepsy, 5 M | 2 | 0.0607 |
| PROSNOT05 | prostate, 67 M, match to PROSTUT03 | 1 | 0.0576 |
| HNT3AZT01 | hNT2 cell line, treated AZ | 3 | 0.0572 |
| BMARNOT03 | bone marrow, 16 M | 2 | 0.0484 |
| BRSTNOT03 | breast, 54 F, match to BRSTTUT | 3 | 0.0441 |
| STOMTUT01 | stomach tumor, 52 M, | 1 | 0.0368 |
| BRAINOT04 | brain, choroid plexus, 44 M | 1 | 0.0356 |
| BRAINOT10 | brain, cerebellum, Alzheimer's, 74 M | 1 | 0.0348 |
| HNT2NOT01 | hNT2 cell line, control | 2 | 0.0345 |
| MMLR3DT01 | macrophages (adher PBMNC), 72-hr MLR | 1 | 0.0332 |
| SPLNFEM01 | spleen, fetal, WM | 1 | 0.0332 |
| BRAINOT14 | brain, 40 F, match BRAITUT12 | 1 | 0.0315 |
| NEUTGMT01 | granulocytes, M/F, treated GM-CSF | 2 | 0.0313 |
| THYRNOT02 | thyroid, hyperthyroidism, 16 F | 1 | 0.0303 |
| BRAINON01 | brain, 26 M, NORM | 3 | 0.0296 |
| TONGTUT01 | tongue tumor, carcinoma, 36 M | 1 | 0.0295 |
| BRAITUT08 | brain tumor, astrocytoma, 47 M | 2 | 0.0293 |
| BEPINOT01 | bronchial epithelium, 54 M | 2 | 0.0289 |
| FIBRSEM01 | fibroblasts, senescent, NORM, WM | 1 | 0.0289 |
| COLNNOT05 | colon, 40 M, match to COLNCRT01 | 1 | 0.0289 |
| STOMTUT02 | stomach tumor, lymphoma, 68 F | 1 | 0.0284 |
| PROSNOT11 | prostate, 28 M | 1 | 0.0282 |
| BRSTTUT02 | breast tumor, 54 F, match BRSTNOT03 | 2 | 0.0279 |
| BLADNOT04 | bladder and seminal vesicle, 28 M | 1 | 0.0278 |
| UTRSNOT05 | uterus, 45 F | 1 | 0.0278 |
| PROSNOT19 | prostate, 59 M | 1 | 0.0272 |
| BRAINOM03 | brain, 55 M, NORM, WM | 1 | 0.0270 |
| ENDCNOT01 | endothelial cells, coronary artery, 58 M | 1 | 0.0268 |
| KIDNTUT01 | kidney tumor, Wilms, 8m F | 1 | 0.0267 |
| PENITUT01 | penis tumor, carcinoma, 64 M | 1 | 0.0267 |
| LNODNOT03 | lymph node, 67 M | 1 | 0.0265 |
| LEUKNOT03 | white blood cells, 27 F | 1 | 0.0262 |
| URETTUT01 | ureter tumor, 69 M | 1 | 0.0262 |
| ENDANOT01 | endothelial cells, aorta, M | 2 | 0.0257 |
| PROSNOT18 | prostate, 58 M | 1 | 0.0256 |
| BRSTTUT08 | breast tumor, 45 F, match to BRSTNOT09 | 1 | 0.0254 |
| SPLNFET02 | spleen, fetal M | 2 | 0.0252 |
| UTRSNOT02 | uterus, 34 F | 3 | 0.0233 |
| PROSNOT06 | prostate, 57 M, match to PROSTUT04 | 2 | 0.0229 |
| NERVMSM01 | multiple sclerosis, 46 M, NORM, WM | 1 | 0.0224 |
| ENDCNOT03 | endothelial cells, neonatal M | 1 | 0.0210 |
| OVARTUT01 | ovarian tumor, 43 F | 2 | 0.0207 |
| UTRPNOM01 | uterus, F, NORM, WM | 1 | 0.0201 |
| LUNGNOT03 | lung, 79 M, match to LUNGTUT02 | 1 | 0.0200 |

FIGURE 4A

| | | | |
|---|---|---|---|
| BRSTNOT04 | breast, 62 F | 2 | 0.0192 |
| BRSTTUT01 | breast tumor, 55 F, match BRSTNOT02 | 2 | 0.0189 |
| HNT2RAT01 | hNT2 cell line, treated RA | 1 | 0.0188 |
| BRAINOT09 | brain, fetal M | 2 | 0.0186 |
| SYNOOAT01 | synovium, knee, osteoarthritis, 82 F | 1 | 0.0180 |
| MMLR2DT01 | macrophages (adher PBMNC), 48-hr MLR | 1 | 0.0178 |
| SINTBST01 | small intestine, ileum, Crohn's, 18 F | 1 | 0.0168 |
| PGANNOT01 | paraganglionic tumor, 46 M | 1 | 0.0160 |
| BRSTNOT05 | breast, 58 F, match to BRSTTUT03 | 2 | 0.0149 |
| CONNNOT01 | fat, mesentery, 71 M | 1 | 0.0149 |
| BRSTNOT07 | breast, 43 F | 1 | 0.0146 |
| NGANNOT01 | ganglioneuroma, 9 M | 2 | 0.0146 |
| COLNFET02 | colon, fetal F | 1 | 0.0143 |
| LUNGFET03 | lung, fetal F | 2 | 0.0138 |
| THYRNOT03 | thyroid tumor, adenoma, 28 F | 1 | 0.0138 |
| LATRTUT02 | heart tumor, myoma, 43 M | 1 | 0.0137 |
| PITUNOT02 | pituitary, 15-75 M/F | 1 | 0.0135 |
| BRAINOM01 | brain, infant F, NORM, WM | 3 | 0.0134 |
| PROSNOT16 | prostate, 68 M | 1 | 0.0132 |
| CONUTUT01 | mesentery tumor, sigmoid, 61 F | 1 | 0.0130 |
| BLADTUT04 | bladder tumor, 60 M, match BLADNOT05 | 1 | 0.0127 |
| PROSTUT04 | prostate tumor, 57 M, match PROSNOT06 | 1 | 0.0117 |
| KIDNNOT05 | kidney, neonatal F | 1 | 0.0106 |
| MELANOM01 | melanocytes, M, NORM, WM | 1 | 0.0096 |
| PROSNON01 | prostate, 28 M, NORM | 1 | 0.0094 |
| BRAITUT02 | brain tumor, metastasis, 58 M | 1 | 0.0075 |
| ISLTNOT01 | pancreas, islet cells, M/F | 1 | 0.0064 |
| LIVSFEM02 | liver/spleen, fetal M, NORM, WM | 2 | 0.0053 |

FIGURE 4B

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 262 amino acids
        ( B ) TYPE: amino acid
        ( C ) STRANDEDNESS: single
        ( D ) TOPOLOGY: linear ( v i i ) IMMEDIATE SOURCE:
        ( A ) LIBRARY: BRAITUT02
        ( B ) CLONE: 762280

( x i ) SEQUENCE DESCRIPTION: SEQ ID NO:1:

```
Met Phe Arg Phe Met Arg Asp Val Glu Pro Glu Asp Pro Met Phe Leu
  1               5                  10                  15
Met Asp Pro Phe Ala Ile His Arg Gln His Met Ser Arg Met Leu Ser
                 20                  25                  30
Gly Gly Phe Gly Tyr Ser Pro Phe Leu Ser Ile Thr Asp Gly Asn Met
             35                  40                  45
Pro Gly Thr Arg Ala Ala Ser Arg Arg Met Gln Gln Ala Gly Ala Val
         50                  55                  60
Xaa Pro Phe Gly Xaa Leu Gly Met Ser Gly Gly Phe Met Asp Met Phe
 65                  70                  75                  80
Gly Met Met Asn Asp Met Xaa Gly Asn Met Glu His Met Thr Ala Gly
                 85                  90                  95
Gly Asn Cys Gln Thr Phe Ser Ser Ser Thr Val Ile Ser Tyr Ser Asn
            100                 105                 110
Thr Gly Asp Gly Ala Pro Lys Val Tyr Gln Glu Thr Ser Glu Met Arg
        115                 120                 125
Ser Ala Pro Gly Gly Ile Arg Glu Thr Arg Arg Thr Val Arg Asp Ser
    130                 135                 140
Asp Ser Gly Leu Glu Gln Met Ser Ile Gly His His Ile Arg Asp Arg
145                 150                 155                 160
Ala His Ile Leu Gln Arg Ser Arg Asn His Arg Thr Gly Asp Gln Glu
                165                 170                 175
Glu Arg Gln Asp Tyr Ile Asn Leu Asp Glu Ser Glu Ala Ala Ala Phe
            180                 185                 190
Asp Asp Glu Trp Arg Arg Glu Thr Ser Arg Phe Arg Gln Gln Arg Pro
        195                 200                 205
Leu Glu Phe Arg Arg Leu Glu Ser Ser Gly Ala Gly Gly Arg Arg Ala
    210                 215                 220
Glu Gly Pro Pro Arg Leu Ala Ile Gln Gly Pro Glu Asp Ser Leu Pro
```

| 225 | | | | 230 | | | | 235 | | | | 240 | | |
|---|---|---|---|---|---|---|---|---|---|---|---|---|---|---|
| Asp | Ser | Pro | Ala | Ala | Met | Thr | Gly | Glu | Gly | Pro | Gly | Ala | Ser | Ala | Leu |
| | | | | 245 | | | | | 250 | | | | | 255 | |

| Leu | Tyr | Arg | Leu | Arg | Gly |
|---|---|---|---|---|---|
| | | | 260 | | |

( 2 ) INFORMATION FOR SEQ ID NO:2:

( i ) SEQUENCE CHARACTERISTICS:
        ( A ) LENGTH: 1322 base pairs
        ( B ) TYPE: nucleic acid
        ( C ) STRANDEDNESS: single
        ( D ) TOPOLOGY: linear ( v i i ) IMMEDIATE SOURCE:
        ( A ) LIBRARY: BRAITUT02
        ( B ) CLONE: 762280

( x i ) SEQUENCE DESCRIPTION: SEQ ID NO:2:

| | | | | | |
|---|---|---|---|---|---|
| GGGGGGCGTA | CGGAGGTGGC | AGCTGTGGGA | GGAGGCGGCG | TGGAAGGCCG | AGGAGCTCAA | 60 |
| GCCCGGACCA | ATCCCCACGT | TCCGGGCCGC | CACCCTGACC | CTGCAGCGTA | CCGGGAAGCG | 120 |
| AAACCGGCCG | GATGGGCCGC | TGAGCCCGAA | TCGGGCACTG | TGTGGAGCCC | CCTGGAGCTG | 180 |
| AGATCAGGAT | GTTCCGCTTC | ATGAGGGACG | TGGAGCCTGA | GGATCCCATG | TTCCTGATGG | 240 |
| ATCCCTTTGC | TATTCACCGT | CAGCATATGA | GCCGTATGTT | GTCAGGTGGC | TTTGGATATA | 300 |
| GCCCCTTCCT | CAGCATCACA | GATGGCAACA | TGCCAGGGAC | CAGGGCTGCC | AGCCGCCGGA | 360 |
| TGCAGCAGGC | TGGAGCTGTC | TNCCCCTTTG | GGNTGCTGGG | AATGTCGGGT | GGTTTCATGG | 420 |
| ACATGTTTGG | GATGATGAAT | GACATGNTTG | GAAACATGGA | ACACATGACA | GCTGGAGGCA | 480 |
| ATTGCCAGAC | CTTCTCATCT | TCCACTGTCA | TCTCCTACTC | CAATACGGGT | GATGGTGCCC | 540 |
| CCAAGGTCTA | CCAAGAGACA | TCAGAGATGC | GCTCGGCACC | AGGCGGGATC | CGGGAGACAC | 600 |
| GGAGGACTGT | TCGGGATTCA | GACAGTGGAC | TGGAGCAGAT | GTCCATTGGG | CATCACATCC | 660 |
| GGGACAGGGC | TCACATCCTC | CAGCGCTCCC | GAAACCATCG | CACGGGGGAC | CAGGAGGAGC | 720 |
| GGCAGGACTA | TATCAACCTG | GATGAGAGTG | AGGCCGCAGC | GTTTGATGAC | GAGTGGCGGC | 780 |
| GGGAGACCTC | CCGATTCCGG | CAGCAGCGTC | CCCTGGAGTT | TCGGCGGCTT | GAGTCCTCAG | 840 |
| GGGCTGGGGG | ACGAAGGGCG | GAGGGGCCTC | CCCGCCTGGC | CATCCAGGGA | CCTGAGGACT | 900 |
| CCCTTCCCGA | CAGTCCCGCC | GCTATGACTG | GTGAGGGCCC | CGGGGCCTCA | GCTCTCTTGT | 960 |
| ACAGGCTGAG | AGGCTGAGAA | ATCATCCCCT | GAATAACTTT | TTCCTCTCGA | TTCCCATCCC | 1020 |
| CAATTTAATA | TTAAATTAAC | AGGCAAGCCG | GCCCCCACCT | CTCCCTGGGG | GTCTCAGGGA | 1080 |
| GAACCTTTCA | CGGCACCCTT | TCCCTACCTT | TTCCTTCTTT | AATCTCCTGG | TTTACCATTG | 1140 |
| ATGACTTCGG | CTCTGCATCT | ACTTACTTGA | TTTTTCATTC | TGCCACTTCA | TCTTCAAACC | 1200 |
| CCCTCACCTT | TCCATCCTA | CTCCTGCCAT | GCATTGAAGG | GTCAATGCAT | TTTGGGGTGA | 1260 |
| GNTTNGGTTT | AGGGGCCCCT | TCATNCCTNA | GCTACCTGGG | TCTTTGCCCA | ACTTTTCTCA | 1320 |
| GA | | | | | | 1322 |

( 2 ) INFORMATION FOR SEQ ID NO:3:

( i ) SEQUENCE CHARACTERISTICS:
        ( A ) LENGTH: 268 amino acids
        ( B ) TYPE: amino acid
        ( C ) STRANDEDNESS: single
        ( D ) TOPOLOGY: linear ( v i i ) IMMEDIATE SOURCE:
        ( A ) LIBRARY: GenBank (B) CLONE: 1066392

(xi) SEQUENCE DESCRIPTION: SEQ ID NO:3:

```
Met Phe Arg Met Leu Asn Ser Ser Phe Glu Asp Asp Pro Phe Phe Ser
 1               5                  10                  15
Glu Ser Ile Leu Ala His Arg Glu Asn Met Arg Gln Met Ile Arg Ser
             20                  25                  30
Phe Ser Glu Pro Phe Gly Arg Asp Leu Leu Ser Ile Ser Asp Gly Arg
         35                  40                  45
Gly Arg Ala His Asn Arg Arg Gly His Asn Asp Gly Glu Asp Ser Leu
     50                  55                  60
Thr His Thr Asp Val Ser Ser Phe Gln Thr Met Asp Gln Met Val Ser
 65                  70                  75                  80
Asn Met Arg Asn Tyr Met Gln Lys Leu Glu Arg Asn Phe Gly Gln Leu
                 85                  90                  95
Ser Val Asp Pro Asn Gly His Ser Phe Cys Ser Ser Ser Val Met Thr
            100                 105                 110
Tyr Ser Lys Ile Gly Asp Glu Pro Pro Lys Val Phe Gln Ala Ser Thr
        115                 120                 125
Gln Thr Arg Arg Ala Pro Gly Gly Ile Lys Glu Thr Arg Lys Ala Met
    130                 135                 140
Arg Asp Ser Asp Ser Gly Leu Glu Lys Met Ala Ile Gly His His Ile
145                 150                 155                 160
His Asp Arg Ala His Val Ile Lys Lys Ser Lys Asn Lys Lys Thr Gly
                165                 170                 175
Asp Glu Glu Val Asn Gln Glu Phe Ile Asn Met Asn Glu Ser Asp Ala
            180                 185                 190
His Ala Phe Asp Glu Glu Trp Gln Ser Glu Val Leu Lys Tyr Lys Pro
        195                 200                 205
Gly Arg His Asn Leu Gly Asn Thr Arg Met Arg Ser Val Gly His Glu
    210                 215                 220
Asn Pro Gly Ser Arg Glu Leu Lys Arg Arg Glu Lys Pro Gln Gln Ser
225                 230                 235                 240
Pro Ala Ile Glu His Gly Arg Arg Ser Asn Val Leu Gly Asp Lys Leu
                245                 250                 255
His Ile Lys Gly Ser Ser Val Lys Ser Asn Lys Lys
            260                 265
```

(2) INFORMATION FOR SEQ ID NO:4:

(i) SEQUENCE CHARACTERISTICS:
        (A) LENGTH: 1116 base pairs
        (B) TYPE: nucleic acid
        (C) STRANDEDNESS: single
        (D) TOPOLOGY: linear (vii) IMMEDIATE SOURCE:
        (A) LIBRARY: GenBank
        (B) CLONE: 1066391

(xi) SEQUENCE DESCRIPTION: SEQ ID NO:4:

```
GTTATGTGTT CCCGTCCGTA CTGGAGGCTA GCTCTTGTCG CGGCCGCGGC GAGTTAACAT      60
CGTTTTTCCA ATCTGTCCGC GGCTGCCGCC ACCCAAGACA GAGCCAGAAT GTTCAGGATG     120
CTGAACAGCA GTTTTGAGGA TGACCCCTTC TTCTCTGAGT CCATTCTTGC ACACCGAGAA     180
AATATGCGAC AGATGATAAG AAGTTTTTCT GAACCCTTTG GAAGAGACTT GCTCAGTATC     240
TCTGATGGTA GAGGGAGAGC TCATAATCGT AGAGGACATA ATGATGGTGA AGATTCTTTG     300
```

```
ACTCATACAG  ATGTCAGCTC  TTTCCAGACC  ATGGACCAAA  TGGTGTCAAA  TATGAGAAAC      360

TATATGCAGA  AATTAGAAAG  AAACTTCGGT  CAACTTTCAG  TGGATCCAAA  TGGACATTCA      420

TTTTGTTCTT  CCTCAGTTAT  GACTTATTCC  AAAATAGGAG  ATGAACCGCC  AAAGGTTTTT      480

CAGGCCTCAA  CTCAAACTCG  TCGAGCTCCA  GGAGGAATAA  AGGAAACCAG  GAAAGCAATG      540

AGAGATTCTG  ACAGTGGACT  AGAAAAAATG  GCTATTGGTC  ATCATATCCA  TGACCGAGCT      600

CATGTCATTA  AAAAGTCAAA  GAACAAGAAG  ACTGGAGATG  AAGAGGTCAA  CCAGGAGTTC      660

ATCAATATGA  ATGAAAGCGA  TGCTCATGCT  TTGATGAGG   AGTGGCAAAG  TGAGGTTTTG      720

AAGTACAAAC  CAGGACGACA  CAATCTAGGA  AACACTAGAA  TGAGAAGTGT  TGGCCATGAG      780

AATCCTGGCT  CCCGAGAACT  TAAAAGAAGG  GAGAAACCTC  AACAAAGTCC  AGCCATTGAA      840

CATGGAAGGA  GATCAAATGT  TTTGGGGGAC  AAACTCCACA  TCAAAGGCTC  ATCTGTGAAA      900

AGCAACAAAA  AATAAATAGC  CATGCATTTG  ATTTGTTTAG  TTTTGATTGT  TTTAACAGTT      960

AGTAATGGTG  CTGGGTAATA  AGCATAAGAC  CAATCTCTTG  CTGTTAAATC  AGTTCTGTCC     1020

TTGGCAACTT  TCTTCTGATA  TCTGAATGTT  CATGAAGGTC  CTAGCTTTAT  ATTGTCCCTC     1080

TTTTAGGAAT  AAAATTTTGA  TTTTCAACAA  AAAAAA                                 1116
```

(2) INFORMATION FOR SEQ ID NO:5:

(i) SEQUENCE CHARACTERISTICS:
        (A) LENGTH: 248 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 1399745

(xi) SEQUENCE DESCRIPTION: SEQ ID NO:5:

```
Met  Phe  Arg  Phe  Met  Arg  Asp  Val  Glu  Pro  Glu  Asp  Pro  Met  Phe  Leu
 1              5                        10                       15

Met  Asp  Pro  Phe  Ala  Ile  His  Arg  Gln  His  Met  Ser  Arg  Met  Leu  Ser
              20                       25                       30

Gly  Gly  Phe  Gly  Tyr  Ser  Pro  Phe  Leu  Ser  Ile  Thr  Asp  Gly  Asn  Met
              35                       40                       45

Pro  Gly  Thr  Arg  Pro  Ala  Ser  Arg  Arg  Met  Gln  Gln  Ala  Gly  Ala  Val
         50                       55                       60

Ser  Pro  Phe  Gly  Met  Leu  Gly  Met  Ser  Gly  Gly  Phe  Met  Asp  Met  Phe
 65                       70                       75                       80

Gly  Met  Met  Asn  Asp  Met  Ile  Gly  Asn  Met  Glu  His  Met  Thr  Ala  Gly
                        85                       90                       95

Gly  Asn  Cys  Gln  Thr  Phe  Ser  Ser  Ser  Thr  Val  Ile  Ser  Tyr  Ser  Asn
                       100                      105                      110

Thr  Gly  Asp  Gly  Ala  Pro  Lys  Val  Tyr  Gln  Glu  Thr  Ser  Glu  Met  Arg
              115                      120                      125

Ser  Ala  Pro  Gly  Gly  Ile  Arg  Glu  Thr  Arg  Arg  Thr  Val  Arg  Asp  Ser
              130                      135                      140

Asp  Ser  Gly  Leu  Glu  Gln  Met  Ser  Ile  Gly  His  His  Ile  Arg  Asp  Arg
145                      150                      155                      160

Ala  His  Ile  Leu  Gln  Arg  Ser  Arg  Asn  His  Arg  Thr  Gly  Asp  Gln  Glu
                       165                      170                      175

Glu  Arg  Gln  Asp  Tyr  Ile  Asn  Leu  Asp  Glu  Ser  Glu  Ala  Ala  Ala  Phe
              180                      185                      190

Asp  Asp  Glu  Trp  Arg  Arg  Glu  Thr  Ser  Arg  Phe  Arg  Gln  Gln  Arg  Pro
```

|   |   |   | 195 |   |   |   |   | 200 |   |   |   |   | 205 |   |   |
|---|---|---|---|---|---|---|---|---|---|---|---|---|---|---|---|
Leu | Glu | Phe | Arg | Arg | Leu | Glu | Ser | Ser | Gly | Ala | Gly | Gly | Arg | Arg | Ala
 | 210 | | | | | 215 | | | | | 220 | | | | |

Glu Gly Pro Pro Arg Leu Ala Ile Gln Gly Pro Glu Asp Ser Pro Ser
225                     230                 235                 240

Arg Gln Ser Arg Arg Tyr Asp Trp
                245

(2) INFORMATION FOR SEQ ID NO:6:

(i) SEQUENCE CHARACTERISTICS:
        (A) LENGTH: 1502 base pairs
        (B) TYPE: nucleic acid
        (C) STRANDEDNESS: single
        (D) TOPOLOGY: linear (vii) IMMEDIATE SOURCE:
        (A) LIBRARY: GenBank
        (B) CLONE: 1399744

(xi) SEQUENCE DESCRIPTION: SEQ ID NO:6:

```
CTCTAAAGGG  CAGCTGTGGG  AGGAGGCGGC  GTGGAAGGCC  GAGGAGCTCA  AGCCCGGACC    60
AATCCCCACG  TTCCGGGCCG  CGACCCTGAC  CCTGCAGCGT  ACCGGGAAGC  GAAACCGGCC   120
GGATGGGCCG  CTGAGCCCGA  ATCGGGCACT  GTGTGGAGCC  CCTGGAGCT   GAGATCAGGA   180
TGTTCCGCTT  CATGAGGGAC  GTGGAGCCTG  AGGATCCCAT  GTTCCTGATG  GATCCCTTTG   240
CTATTCACCG  TCAGCATATG  AGCCGTATGT  TGTCAGGTGG  CTTTGGATAT  AGCCCCTTCC   300
TCAGCATCAC  AGATGGCAAC  ATGCCAGGGA  CCAGGCCTGC  CAGCCGCCGG  ATGCAGCAGG   360
CTGGAGCTGT  CTCCCCCTTT  GGGATGCTGG  GAATGTCGGG  TGGTTTCATG  ACATGTTTG    420
GGATGATGAA  TGACATGATT  GGAAACATGG  AACACATGAC  AGCTGGAGGC  AATTGCCAGA   480
CCTTCTCATC  TTCCACTGTC  ATCTCCTACT  CCAATACGGG  TGATGGTGCC  CCCAAGGTCT   540
ACCAAGAGAC  ATCAGAGATG  CGCTCGGCAC  CAGGCGGGAT  CCGGGAGACA  CGGAGGACTG   600
TTCGGGATTC  AGACAGTGGA  CTGGAGCAGA  TGTCCATTGG  GCATCACATC  CGGGACAGGG   660
CTCACATCCT  CCAGCGCTCC  CGAAACCATC  GCACGGGGGA  CCAGGAGGAG  CGGCAGGACT   720
ATATCAACCT  GGATGAGAGT  GAGGCCGCAG  CGTTTGATGA  CGAGTGGCGG  CGGGAGACCT   780
CCCGATTCCG  GCAGCAGCGT  CCCCTGGAGT  TTCGGCGGCT  TGAGTCCTCA  GGGGCTGGGG   840
GACGAAGGGC  GGAGGGGCCT  CCCCGCCTGG  CCATCCAGGG  ACCTGAGGAC  TCCCCTTCCC   900
GACAGTCCCG  CCGCTATGAC  TGGTGAGGGC  CCCGGGCCCT  CAGCCTCTCT  TGTACAGGCT   960
GAGAGGCTGA  GAAATCATCC  CCTGAATAAC  TTTTTCCTCT  CGATTCCCAT  CCCCAATTTA  1020
ATATTAAATT  AACAGGCAAG  CCGGCCCCCA  CCTCTCCCTG  GGGGTCTCAG  GGAGAACCTT  1080
TCACGGCACC  CTTTCCCTAC  CTTTTCCTTC  TTTAATCTCC  TGGTTTACCA  TTGATGACTT  1140
CGCCTCTGCA  TCTACTGACT  TGATTTTTCA  TTCTGCCACT  CCATCTTCAA  ACCCCCTCAC  1200
CTTTCCCATC  CTACTCCTGC  CATGCATTGA  AGGGTCAATG  CATTTTGGGG  TGAGCTCTGG  1260
GTTTAGGGGC  CCCCTCCATC  CCTCAGCTAC  CCTGGATCTT  TGCCCACCTC  TTCCTCAGAG  1320
CCCCCACTGA  GGGGCCGTAG  CCCTATCTAG  GGCTGTGGAA  GGAGCAGACT  GGTTCCTAAC  1380
TCTCTCCCTC  CTCCTGCCCA  CACACATCAA  AAGAATCTTC  CCTACACCCT  TCTCTGCCTT  1440
TATTTTTTGA  TTTGTGCAAC  TTGTAACTAG  GTGTTTATGG  AATAAAGGAG  AATGGAAAAA  1500
AG                                                                     1502
```

HUMAN MLF3 PROTEIN

FIELD OF THE INVENTION

This invention relates to nucleic acid and amino acid sequences of a novel human protein, MLF3, and to the use of these sequences in the diagnosis, prevention, and treatment of disease.

BACKGROUND OF THE INVENTION

The MLF (myelodysplasia/myeloid leukemia factor) gene family comprises the MLF1 and MLF2 genes which encode cytoplasmic proteins. Rearrangement of the MLF1 gene is observed in patients with myelodysplastic syndrome and acute myeloid leukemia (AML); myelodysplastic syndrome precedes AML in certain cases. The t(3:5)(q25.1;q34) chromosomal translocation, a non-random translocation which appears to be restricted to myelodysplastic syndrome and AML, creates a fusion between sequences of the nucleophosmin (NPM) gene and the MLF1 gene. This rearrangement results in the expression of a fusion protein whose amino-terminal end contains most of the structural motifs of the NPM protein, including a nuclear localization signal, fused to residues 17–268 of the MLF1 protein. The NPM-MLF1 fusion protein localizes to the nucleus, with highest levels seen in the nucleolus [Yoneda-Kato, N. et al. (1996) Oncogene 12:265]. Identical fusion junctions were found in three AML patients suggesting that the NPM-MLF1 fusion protein is involved in the events that lead to the clonal disruption of hematopoietic cell development characteristic of the myelodysplastic and leukemic phases of AML (Yoneda-Kato, N. et al., supra). The MLF1 gene is normally expressed in a variety of tissues with the highest levels of expression seen in testis, ovary, skeletal and cardiac muscle, colon and kidney. Low levels or no expression of MLF1 is seen in spleen, thymus and peripheral blood leukocytes.

The MLF2 gene encodes a protein which is highly related (40% identity, 63% similarity) to the MLF1 protein (Kuefer, M. U. et al. (1996) Genomics 35:392). The MLF2 gene is ubiquitously expressed in contrast to the tissue-restricted pattern of expression displayed by the MLF1 gene. The MLF2 gene maps to human chromosome 12p13, a region frequently involved in deletions and translocations in acute myeloid and lymphoid leukemias (Kuefer, M. U. et al., supra).

The discovery of molecules related to the MLF gene family satisfies a need in the art by providing new diagnostic or therapeutic compositions useful in the treatment of disorders associated with alterations in the expression of members of the MLF gene family.

SUMMARY OF THE INVENTION

The present invention features a novel protein hereinafter designated MLF3 and characterized as having similarity to the human MLF1 and MLF2 proteins.

Accordingly, the invention features a substantially purified polypeptide having the amino acid sequence shown in SEQ ID NO:1 or fragments thereof. Preferred fragments of SEQ ID NO:1 are fragments of about 15 amino acids or greater in length which define fragments unique (i.e., having less than about 25% identity to fragments of another protein) to SEQ ID NO:1 or which retain biological activity or immunological activity (i.e., capable of eliciting anti-MLF3 antibodies). Fragments of SEQ ID NO:1 which are at least 25 amino acids, at least 50 amino acids, at least 100 amino acids, at least 125 amino acids, at least 200 amino acids and at least 250 amino acids in length are contemplated.

The present invention further provides isolated and substantially purified polynucleotide sequences encoding the polypeptide comprising the amino acid sequence of SEQ ID NO:1 or fragments thereof. In a particular aspect, the polynucleotide is the nucleotide sequence of SEQ ID NO:2 or variants thereof. In another embodiment, the present invention provides polynucleotides comprising fragments of SEQ ID NO:2 having a length greater than 20 nucleotides. The invention further contemplates fragments of this polynucleotide sequence (i.e., SEQ ID NO:2) that are at least 50 nucleotides, at least 100 nucleotides, at least 250 nucleotides, at least 500 nucleotides and at least 950 nucleotides in length.

In addition, the invention provides polynucleotide sequences which hybridize under stringent conditions to the polynucleotide sequence of SEQ ID NO:2. In another embodiment the present invention provides a composition comprising an isolated and purified polynucleotide sequence encoding MLF3.

The invention provides polynucleotide sequences comprising the complement of SEQ ID NO:2 or variants thereof; these complementary nucleic acid sequences may comprise the complement of the entire nucleic acid sequence of SEQ ID NO:2 or fragments thereof. In another embodiment the present invention provides a composition comprising an isolated and purified polynucleotide sequence comprising the complement of SEQ ID NO:2 or variants thereof.

The invention additionally features nucleic acid sequences encoding polypeptides, oligonucleotides, peptide nucleic acids (PNA), fragments, portions or antisense molecules thereof, and expression vectors and host cells comprising polynucleotides that encode MLF3.

In another embodiment the present invention provides an isolated polynucleotide comprising at least a portion of the nucleic acid sequence of SEQ ID NO:2 or variants thereof contained on a recombinant expression vector. In yet another embodiment, the expression vector containing the polynucleotide sequence is contained within a host cell. The invention is not limited by the nature of the host cell employed. For example, the host cell may be an E. coli cell, a yeast cell, an insect cell, a mammalian cell, etc.

The present invention also provides a method for producing a polypeptide comprising the amino acid sequence of SEQ ID NO:1 or fragments thereof, the method comprising the steps of: a) culturing the host cell containing an expression vector containing an isolated polynucleotide encoding at least a fragment of the MLF3 polypeptide under conditions suitable for the expression of the polypeptide; and b) recovering the polypeptide from the host cell culture.

In another embodiment, the invention provides a pharmaceutical composition comprising a substantially purified human MLF3 protein having the amino acid sequence of SEQ ID NO:1 in conjunction with a suitable pharmaceutical carrier.

The invention also provides a purified antibody which binds specifically to a polypeptide comprising at least a portion of the amino acid sequence of SEQ ID NO:1.

Still further, the invention provides a purified agonist which specifically binds to and modulates the activity of a polypeptide comprising at least a portion of the amino acid sequence of SEQ ID NO:1. The present invention further provides a pharmaceutical composition comprising a purified agonist which specifically binds to and modulates the activity of a polypeptide comprising at least a portion of the amino acid sequence of SEQ ID NO:1. In another embodiment, the invention provides a purified antagonist which specifically binds to and modulates the activity of a polypeptide comprising at least a portion of the amino acid sequence of SEQ ID NO:1. The present invention further provides a pharmaceutical composition comprising a purified antagonist which specifically binds to and modulates the activity of a polypeptide comprising at least a portion of the amino acid sequence of SEQ ID NO:1.

The invention also provides a method for treating breast cancer comprising administering to a subject in need of such treatment an effective amount of a pharmaceutical composition comprising a purified antagonist which specifically binds to and modulates the activity of a polypeptide comprising at least a portion of the amino acid sequence of SEQ ID NO:1. The treatment of a variety of tumors, including but not limited to brain, stomach, paraganglionic tumors, using agonists as well as antagonists of MLF3 is also contemplated by the present invention.

The invention also provides a method for the detection of polynucleotides encoding human MLF3 in a biological sample comprising the steps of: a) hybridizing a polynucleotide sequence encoding human MLF3 (SEQ ID NO:1) to nucleic acid material of a biological sample, thereby forming a hybridization complex; and b) detecting the hybridization complex, wherein the presence of the complex correlates with the presence of a polynucleotide encoding human MLF3 in the biological sample. In a preferred embodiment, prior to hybridization, the nucleic acid material of the biological sample is amplified by the polymerase chain reaction. In another preferred embodiment, the nucleic acid material comprises metaphase chromosomes prepared from human cells (e.g., from a biopsy or blood sample) and detection of the hybridization complex indicates the chromosomal location (i.e., normal or rearranged) of the MLF3 gene in the human cells.

BRIEF DESCRIPTION OF THE FIGURES

FIGS. 1A–1D show the amino acid sequence (SEQ ID NO:1) and nucleic acid sequence (SEQ ID NO:2) of MLF3. The alignment was produced using MACDNASIS PRO™ software (Hitachi Software Engineering Co., Ltd., San Bruno, Calif.).

FIG. 2 shows the amino acid sequence alignments among MLF3 (SEQ ID NO:1) MLF1 (GI 1066392: SEQ ID NO:3) and MLF2 (GI 1399745; SEQ ID NO:5). The alignment was produced using the multisequence alignment program of DNASTAR™ software (DNASTAR Inc, Madison Wis.).

FIGS. 4A and 4B show the northern analysis for SEQ ID NO:1. The northern analysis was produced electronically using LIFESEQ-FL™ database (Incyte Pharmaceuticals, Inc., Palo Alto, Calif.).

DESCRIPTION OF THE INVENTION

Figure 3A:
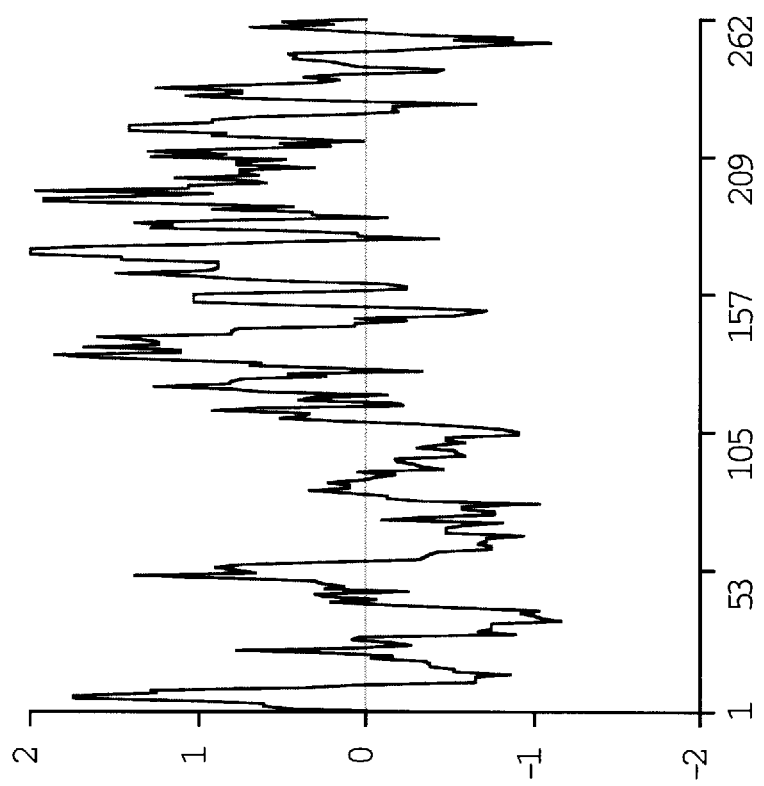
FIGS. 3A, 3B and 3C show the hydrophobicity plots (MACDNASIS PRO software) for MLF3 (SEQ ID NO:1), MLF2 (SEQ ID NO:5), and MLF1 (SEQ ID NO:3), respectively. The positive X axis reflects amino acid position, and the negative Y axis, hydrophobicity.

Before the present proteins, nucleotide sequences, and methods are described, it is understood that this invention is not limited to the particular methodology, protocols, cell lines, vectors, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

Definitions

"Nucleic acid sequence", as used herein, refers to an oligonucleotide, nucleotide, or polynucleotide, and fragments or portions thereof, and to DNA or RNA of genomic or synthetic origin which may be single- or double-stranded, and represent the sense or antisense strand. Similarly, "amino acid sequence" as used herein refers to an oligopeptide, peptide, polypeptide, or protein sequence, and fragments or portions thereof, and to naturally occurring or synthetic molecules.

A "composition comprising a given polynucleotide sequence" as used herein refers broadly to any composition containing the given polynucleotide sequence. The composition may comprise an aqueous solution. Compositions comprising polynucleotide sequences encoding MLF3 (SEQ ID NO:1) or fragments thereof (e.g., SEQ ID NO:2 and fragments thereof) may be employed as hybridization probes. In this case, the MLF3-encoding polynucleotide sequences are typically employed in an aqueous solution containing salts (e.g., NaCl), detergents (e.g., SDS) and other components (e.g., Denhardt's solution, dry milk, salmon sperm DNA, etc.).

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

"Peptide nucleic acid", as used herein, refers to a molecule which comprises an oligomer to which an amino acid residue, such as lysine, and an amino group have been added. These small molecules, also designated anti-gene agents, stop transcript elongation by binding to their complementary strand of nucleic acid (Nielsen, P. E. et al. (1993) Anticancer Drug Des. 8:53–63).

MLF3, as used herein, refers to the amino acid sequences of substantially purified MLF3 obtained from any species, particularly mammalian, including bovine, ovine, porcine, murine, equine, and preferably human, from any source whether natural, synthetic, semi-synthetic, or recombinant.

"Consensus", as used herein, refers to a nucleic acid sequence which has been resequenced to resolve uncalled bases, or which has been extended using XL-PCR™ (Perkin Elmer, Norwalk, Conn.) in the 5' and/or the 3' direction and resequenced, or which has been assembled from the overlapping sequences of more than one Incyte clone using the GELVIEW™ Fragment Assembly system (GCG, Madison, Wis.), or which has been both extended and assembled.

A "variant" of MLF3, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Similar minor variations may also include amino acid deletions or insertions, or both. Guidance in determining which amino acid residues may be substituted, inserted, or deleted without abolishing biological or immunological activity may be found using computer programs well known in the art, for example, DNASTAR software.

A "deletion", as used herein, refers to a change in either amino acid or nucleotide sequence in which one or more amino acid or nucleotide residues, respectively, are absent.

An "insertion" or "addition", as used herein, refers to a change in an amino acid or nucleotide sequence resulting in the addition of one or more amino acid or nucleotide residues, respectively, as compared to the naturally occurring molecule.

A "substitution", as used herein, refers to the replacement of one or more amino acids or nucleotides by different amino acids or nucleotides, respectively.

The term "biologically active", as used herein, refers to a protein having structural, regulatory, or biochemical functions of a naturally occurring molecule. Likewise, "immunologically active" refers to the capability of the natural, recombinant, or synthetic MLF3, or any oligopeptide thereof, to induce a specific immune response in appropriate animals or cells and to bind with specific antibodies.

The term "agonist", as used herein, refers to a molecule which, when bound to MLF3, causes a change in MLF3 which modulates the activity of MLF3. Agonists may include proteins, nucleic acids, carbohydrates, or any other molecules which bind to MLF3.

The terms "antagonist" or "inhibitor", as used herein, refer to a molecule which, when bound to MLF3, blocks or modulates the biological or immunological activity of MLF3. Antagonists and inhibitors may include proteins, nucleic acids, carbohydrates, or any other molecules which bind to MLF3.

The term "modulate", as used herein, refers to a change or an alteration in the biological activity of MLF3. Modulation may be an increase or a decrease in protein activity, a change in binding characteristics, or any other change in the biological, functional, or immunological properties of MLF3.

The term "mimetic", as used herein, refers to a molecule, the structure of which is developed from knowledge of the structure of MLF3 or portions thereof and, as such, is able to effect some or all of the actions of MLF3-like molecules.

The term "derivative", as used herein, refers to the chemical modification of a nucleic acid encoding MLF3 or the encoded MLF3. Illustrative of such modifications would be replacement of hydrogen by an alkyl, acyl, or amino group. A nucleic acid derivative would encode a polypeptide which retains essential biological characteristics of the natural molecule.

The term "substantially purified", as used herein, refers to nucleic or amino acid sequences that are removed from their natural environment, isolated or separated, and are at least 60% free, preferably 75% free, and most preferably 90% free from other components with which they are naturally associated.

"Amplification", as used herein, refers to the production of additional copies of a nucleic acid sequence and is generally carried out using polymerase chain reaction (PCR) technologies well known in the art (Dieffenbach, C. W. and G. S. Dveksler (1995) *PCR Primer, a Laboratory Manual*, Cold Spring Harbor Press, Plainview, N.Y.).

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., membranes, filters, chips, pins or glass slides to which cells have been fixed for in situ hybridization).

The terms "complementary" or "complementarity", as used herein, refer to the natural binding of polynucleotides under permissive salt and temperature conditions by base-pairing. For example, the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands.

The term "homology", as used herein, refers to a degree of complementarity. There may be partial homology or complete homology (i.e., identity). A partially complementary sequence is one that at least partially inhibits an identical sequence from hybridizing to a target nucleic acid; it is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or probe will compete for and inhibit the binding (i.e., the hybridization) of a completely homologous sequence or probe to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding, the probe will not hybridize to the second non-complementary target sequence.

As known in the art, numerous equivalent conditions may be employed to comprise either low or high stringency conditions. Factors such as the length and nature (DNA, RNA, base composition) of the sequence, nature of the target (DNA, RNA, base composition, presence in solution or immobilization, etc.), and the concentration of the salts and other components (e.g., the presence or absence of formamide, dextran sulfate and/or polyethylene glycol) are considered and the hybridization solution may be varied to generate conditions of either low or high stringency different from, but equivalent to, the above listed conditions.

The term "stringent conditions", as used herein, is the "stringency" which occurs within a range from about Tm−5° C. (5° C. below the melting temperature (Tm) of the probe) to about 20° C. to 25° C. below Tm. As will be understood by those of skill in the art, the stringency of hybridization may be altered in order to identify or detect identical or related polynucleotide sequences. Under "stringent conditions" SEQ ID NO:2 or fragments thereof will hybridize to its exact complement and closely related sequences. The stringent conditions are chosen such that SEQ ID NO:2 or fragments thereof will hybridize to sequences encoding human MLF3 but not to sequences encoding human MLF1 (i.e., SEQ ID NO:4 or its RNA equivalents) or MLF2 (SEQ ID NO:6 or its RNA equivalents). When fragments of SEQ ID NO:2 are employed in hybridization reactions, the stringent conditions include the choice of fragments of SEQ ID NO:2 to be used. Fragments of SEQ ID NO:2 which contain unique sequences (i.e., regions which are either non-homologous to or which contain less than about 50% homology or complementarity with SEQ ID NOS:4 and 6) are preferentially employed. SEQ ID NO:4 represents DNA sequences encoding the human MLF1 protein; this DNA sequence can be found in GenBank under accession number 1066391. SEQ ID NO:6 represents DNA sequences encoding the human MLF2 protein; this DNA sequence can be found in GenBank under accession number 1399744.

The term "antisense", as used herein, refers to nucleotide sequences which are complementary to a specific DNA or RNA sequence. The term "antisense strand" is used in reference to a nucleic acid strand that is complementary to the "sense" strand. Antisense molecules may be produced by any method, including synthesis by ligating the gene(s) of interest in a reverse orientation to a viral promoter which permits the synthesis of a complementary strand. Once introduced into a cell, this transcribed strand combines with natural sequences produced by the cell to form duplexes. These duplexes then block either the further transcription or translation. In this manner, mutant phenotypes may be generated. The designation "negative" is sometimes used in reference to the antisense strand, and "positive" is sometimes used in reference to the sense strand.

The term "portion", as used herein, with regard to a protein (as in "a portion of a given protein") refers to fragments of that protein. The fragments may range in size from four amino acid residues to the entire amino acid sequence minus one amino acid. Thus, a protein "comprising at least a portion of the amino acid sequence of SEQ ID NO:1" encompasses the full-length human MLF3 and fragments thereof.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

The term "antigenic determinant", as used herein, refers to that portion of a molecule that makes contact with a particular antibody (i.e., an epitope). When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The terms "specific binding" or "specifically binding", as used herein, in reference to the interaction of an antibody and a protein or peptide, mean that the interaction is dependent upon the presence of a particular structure (i.e., the antigenic determinant or epitope) on the protein; in other words, the antibody is recognizing and binding to a specific protein structure rather than to proteins in general. For example, if an antibody is specific for epitope "A", the presence of a protein containing epitope A (or free, unlabeled A) in a reaction containing labeled "A" and the antibody will reduce the amount of labeled A bound to the antibody.

The term "sample", as used herein, is used in its broadest sense. A biological sample suspected of containing nucleic acid encoding MLF3 or fragments thereof may comprise a cell, chromosomes isolated from a cell (e.g., a spread of metaphase chromosomes), genomic DNA (in solution or bound to a solid support such as for Southern analysis), RNA (in solution or bound to a solid support such as for northern analysis), cDNA (in solution or bound to a solid support), an extract from cells or a tissue, and the like.

The term "correlates with expression of a polynucleotide", as used herein, indicates that the detection of the presence of ribonucleic acid that is similar to SEQ ID NO:2 by northern analysis is indicative of the presence of mRNA encoding MLF3 in a sample and thereby correlates with expression of the transcript from the polynucleotide encoding the protein.

"Alterations" in the polynucleotide of SEQ ID NO:2, as used herein, comprise any alteration in the sequence of polynucleotides encoding MLF3 including deletions, insertions, and point mutations that may be detected using hybridization assays. Included within this definition is the detection of alterations to the genomic DNA sequence which encodes MLF3 (e.g., by alterations in the pattern of restriction fragment length polymorphisms capable of hybridizing to SEQ ID NO:2), the inability of a selected fragment of SEQ ID NO:2 to hybridize to a sample of genomic DNA (e.g., using allele-specific oligonucleotide probes), and improper or unexpected hybridization, such as hybridization to a locus other than the normal chromosomal locus for the polynucleotide sequence encoding MLF3 (e.g., using fluorescent in situ hybridization [FISH] to metaphase chromosomes spreads).

As used herein, the term "antibody" refers to intact molecules as well as fragments thereof, such as Fa, F(ab')$_2$, and Fv, which are capable of binding the epitopic determinant. Antibodies that bind MLF3 polypeptides can be prepared using intact polypeptides or fragments containing small peptides of interest as the immunizing antigen. The polypeptide or peptide used to immunize an animal can be derived from the transition of RNA or synthesized chemically, and can be conjugated to a carrier protein, if desired. Commonly used carriers that are chemically coupled to peptides include bovine serum albumin and thyroglobulin. The coupled peptide is then used to immunize the animal (e.g., a mouse, a rat, or a rabbit).

The term "humanized antibody", as used herein, refers to antibody molecules in which amino acids have been replaced in the non-antigen binding regions in order to more closely resemble a human antibody, while still retaining the original binding ability.

The Invention

The invention is based on the discovery of a novel human protein (MLF3), the polynucleotides encoding MLF3, and the use of these compositions for the diagnosis, prevention, or treatment of diseases associated with altered or abnormal MLF3 expression. As mRNA encoding MLF3 is found in a number of tumors, MLF3 serves as a marker for cancerous cells, particularly breast, brain, stomach and paraganglionic tumor cells. In addition, MLF3 is expressed at the highest levels in brain and therefore serves as a marker for brain tissue.

Nucleic acids encoding the human MLF3 of the present invention were first identified in Incyte Clone 762280 from the BRAITUT02 cDNA library through a computer-generated search for amino acid sequence alignments. A consensus sequence, SEQ ID NO:2, was derived from the following overlapping and/or extended nucleic acid sequences: Incyte Clones 762280 (BRAITUT02), 912942 (STOMNOT02), 896085 (BRSTNOT05), 892034 (STOMTUT01), 774094 (COLONNOT05), 728689 (LUNGNOT03), 720563 (SYNOOAT01), 644216 (BRSTTUT02), 620396 (PGANNOT01), 1291517 (BRAINOT11), 1266914 (BRAINOT09), 1261396 (SYNORAT05), 1253043 (LUNGFET03) and 1219407 (NEUTGMT01).

In one embodiment, the invention encompasses a polypeptide comprising the amino acid sequence of SEQ ID NO:1, as shown in FIGS. 1A and 1B. MLF3 is 262 amino acids in length and contains a single cysteine residue (i.e., $C_{99}$). In addition to providing sites for disulfide bond formation, cysteine residues provide potential sites for palmitoylation. The human MLF3 of the present invention contains sequences which closely match an aminoacyl-transfer RNA synthetases class-II signature motif [Schimmel P (1987) Annu. Rev. Biochem. 56:125] (i.e., residues 192–215 and 196–215 of SEQ ID NO:1). MLF3 contains a sequence (i.e., residues 71–75) which closely matches the serine active site consensus sequence GDSGG found in serine proteases from the trypsin family [Brenner, S. (1988) Nature 334:528]. MLF3 contains a potential C-terminal amidation site (i.e., residues 220–223), a potential cAMP- and cGMP-dependent protein kinase phosphorylation site (i.e., residues 197–200), four potential casein kinase II phosphorylation sites (i.e., residues 42–45, 140–143, 146–149 and 238–241) and four potential protein kinase C phosphorylation sites (i.e., residues 55–57, 137–139, 140–142 and 200–202). MLF3 contains a potential glycosaminoglycan attachment site (i.e., residues 217–220) and 6 potential N-myristoylation sites (i.e., residues 46–51, 50–55, 71–76, 97–102, 133–138 and 220–225); these sites are located internally to MLF3 and therefore proteolytic processing which exposes an internal glycine would be a prerequisite to N-myristoylation of MLF3.

MLF3 contains a stretch of amino acid residues (residues 118–199 of SEQ ID NO:1) which share homology (27% identity and 43% similarity) with the *Trichomonas vaginalis* cysteine protease (TVCYSP) which is proposed to play a role in the pathogenesis of *T. vaginalis* infection (Garber, G. E. et al. (1993) Appl. Parasitol. 34:245). Homology to TVCYSP is also seen in MLF1 (residues 121–202 of SEQ ID NO:3) and MLF2 (residues 118–199 of SEQ ID NO:5) (Kuefer, M. U. et al., supra).

MLF3 contains a stretch of 35 amino acid residues (residues 128–162 of SEQ ID NO:1) which is highly conserved between MLF1 and MLF2 and has been proposed to represent a motif of functional importance (Kuefer, M. U. et al., supra).

Figure 3B:
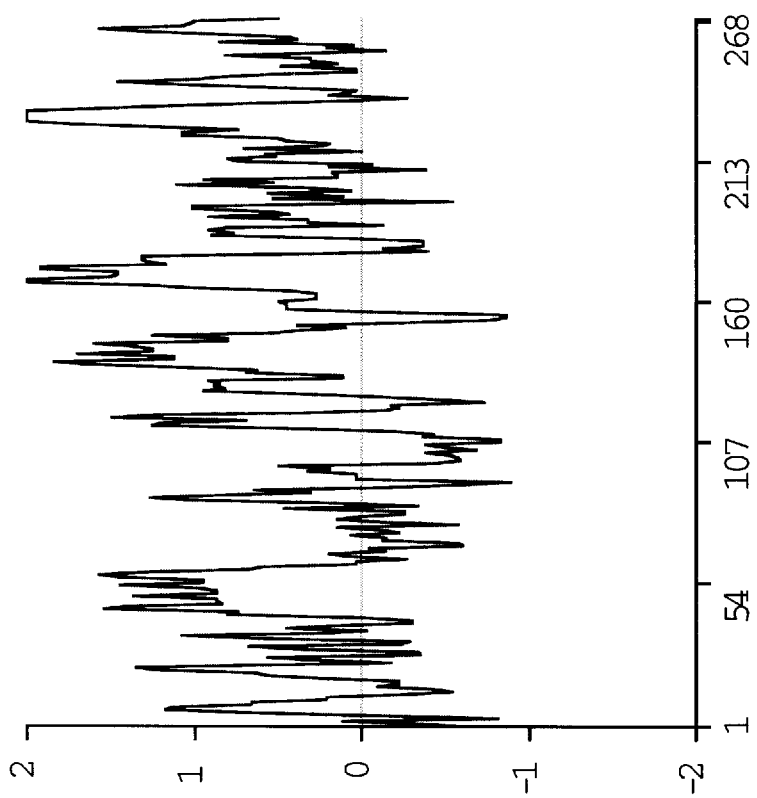
Figure 3C:
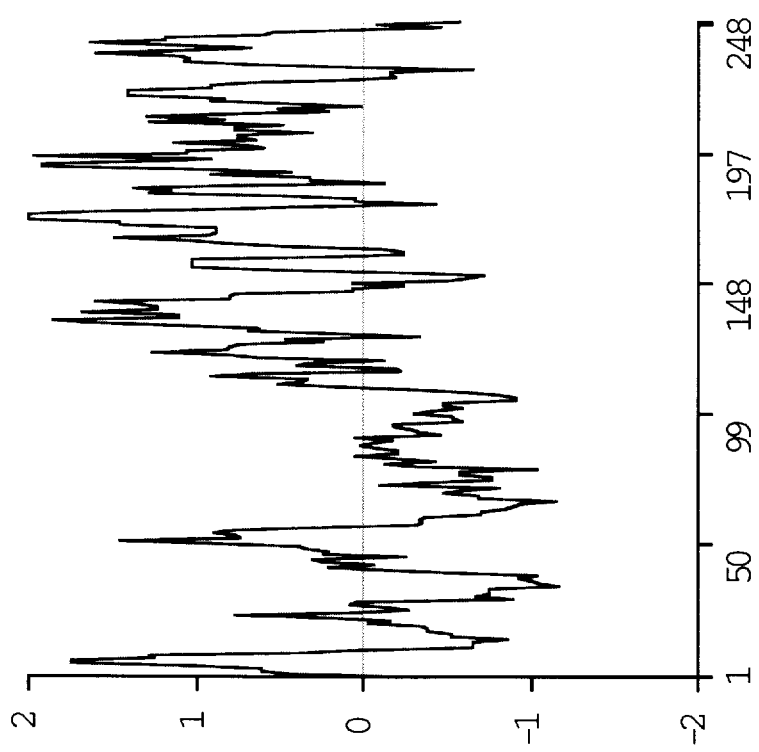

The MLF3 protein of the present invention, like the human MLF2 protein, has an acidic isoelectric point (pI) (MLF3 has a pI of 6.0 and MLF2 has a pI of 6.45). In addition, the MLF3 protein of the present invention, like the human MLF1 and MLF2 proteins, has a high content of arginine residues (MLF3 contains 11.5% arginine; MLF2 contains 12.5% arginine; MLF1 contains 9% arginine). As illustrated by FIGS. 3A, 3B, and 3C, MLF3, MLF1 and MLF2 have similar hydrophobicity plots, with the plots of MLF3 (FIG. 3A) and MLF2 (FIG. 3B) showing the most similarity.

Figure 2B:
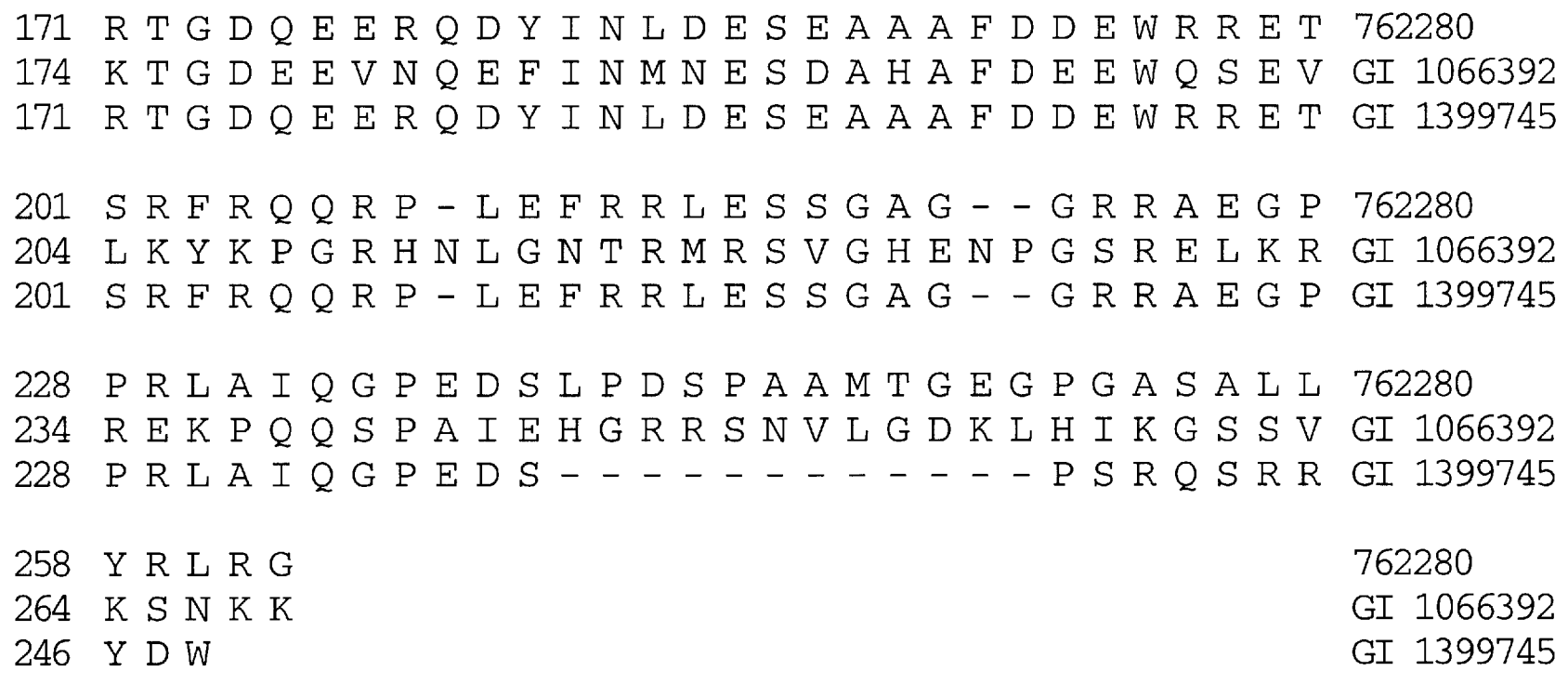

MLF3 has chemical and structural homology with the human MLF1 (GI 1066392; SEQ ID NO:3) and MLF2 (GI 1399745; SEQ ID NO:5) proteins (Yoneda-Kato, N. et al., supra and Kuefer, M. U. et al., supra). In particular, MLF3 and MLF1 share 35% identity and 53% similarity and MLF3 and MLF2 share 89% identity. A pair of residues are said to be similar if they represent conservative substitutions. FIG. 2 provides an alignment between the amino acid sequences of SEQ ID NOS:1, 3 and 5.

Northern analysis (FIGS. 4A and 4B) shows the expression of MLF3-encoding sequences in various libraries, at least 29% of which are cancerous or immortalized and at least 12% of which are involved with the hematopoietic system and/or immune response, including inflammatory and/or autoimmune disease (e.g., Crohn's disease). Of particular note is the expression of MLF3 mRNA in breast tumor (3/77), brain tumor (2/77), stomach tumor (2/77) and paraganglionic tumor (2/77) libraries. This pattern of expression demonstrates that MLF3 serves as a marker for cancerous cells, particularly breast tumor cells. In addition to its expression in a variety of tumors, MLF3 is highly expressed in brain and thus serves as a marker for this tissue. At least 15% of the libraries containing sequences derived from MLF3 mRNA are derived from either normal or diseased brain tissue and at least 11% of the libraries containing MLF3 sequences are derived from cells or tissues in the hematopoietic lineages.

The invention also encompasses MLF3 variants. A preferred MLF3 variant is one having at least 80%, and more preferably 90%, amino acid sequence similarity to the MLF3 amino acid sequence (SEQ ID NO:1). A most preferred MLF3 variant is one having at least 95% amino acid sequence similarity to SEQ ID NO:1.

The invention also encompasses polynucleotides which encode MLF3. Accordingly, any nucleic acid sequence which encodes the amino acid sequence of MLF3 can be used to generate recombinant molecules which express MLF3. In a particular embodiment, the invention encompasses the polynucleotide comprising the nucleic acid sequence of SEQ ID NO:2 as shown in FIGS. 1A and 1B.

It will be appreciated by those skilled in the art that as a result of the degeneracy of the genetic code, a multitude of nucleotide sequences encoding MLF3, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring MLF3, and all such variations are to be considered as being specifically disclosed.

Although nucleotide sequences which encode MLF3 and its variants are preferably capable of hybridizing to the nucleotide sequence of the naturally occurring MLF3 under appropriately selected conditions of stringency, it may be advantageous to produce nucleotide sequences encoding MLF3 or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding MLF3 and its derivatives without altering the encoded amino acid sequences include the production of RNA transcripts having more desirable properties, such as a greater half-life, than transcripts produced from the naturally occurring sequence.

The invention also encompasses production of DNA sequences, or portions thereof, which encode MLF3 and its derivatives, entirely by synthetic chemistry. After production, the synthetic sequence may be inserted into any of the many available expression vectors and cell systems using reagents that are well known in the art at the time of the filing of this application. Moreover, synthetic chemistry may be used to introduce mutations into a sequence encoding MLF3 or any portion thereof.

Also encompassed by the invention are polynucleotide sequences that are capable of hybridizing to the claimed nucleotide sequences, and in particular, those shown in SEQ ID NO:2, under various conditions of stringency. Hybridization conditions are based on the melting temperature (Tm) of the nucleic acid binding complex or probe, as taught in Wahl, G. M. and S. L. Berger (1987; Methods Enzymol. 152:399–407) and Kimmel, A. R. (1987; Methods Enzymol. 152:507–511), and may be used at a defined stringency.

Altered nucleic acid sequences encoding MLF3 which are encompassed by the invention include deletions, insertions, or substitutions of different nucleotides resulting in a polynucleotide that encodes the same or a functionally equivalent MLF3. The encoded protein may also contain deletions, insertions, or substitutions of amino acid residues which produce a silent change and result in a functionally equivalent MLF3. Deliberate amino acid substitutions may be made on the basis of similarity in polarity, charge, solubility, hydrophobicity, hydrophilicity, and/or the amphipathic nature of the residues as long as the biological activity of MLF3 is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine; glycine and alanine; asparagine and glutamine; serine and threonine; phenylalanine and tyrosine.

Also included within the scope of the present invention are alleles of the genes encoding MLF3. As used herein, an "allele" or "allelic sequence" is an alternative form of the gene which may result from at least one mutation in the nucleic acid sequence. Alleles may result in altered mRNAs or polypeptides whose structure or function may or may not be altered. Any given gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

Methods for DNA sequencing which are well known and generally available in the art may be used to practice any embodiments of the invention. The methods may employ such enzymes as the Klenow fragment of DNA polymerase I, SEQUENASE® (US Biochemical Corp, Cleveland, Ohio), Taq polymerase (Perkin Elmer), thermostable T7 polymerase (Amersham, Chicago, Ill.), or combinations of recombinant polymerases and proofreading exonucleases such as the ELONGASE Amplification System marketed by Gibco BRL (Gaithersburg, Md.). Preferably, the process is automated with machines such as the Hamilton MICRO LAB 2200 (Hamilton, Reno, Nev.), Peltier Thermal Cycler (PTC200; MJ Research, Watertown, Mass.) and the ABI 377 DNA sequencers (Perkin Elmer).

The nucleic acid sequences encoding MLF3 may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318–322). In particular, genomic DNA is first amplified in the presence of primer to linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using OLIGO 4.06 Primer Analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1:111–119). In this method, multiple restriction enzyme digestions and ligations may also be used to place an engineered double-stranded sequence into an unknown portion of the DNA molecule before performing PCR.

Another method which may be used to retrieve unknown sequences is that of Parker, J. D. et al. (1991; Nucleic Acids Res. 19:3055–3060). Additionally, one may use PCR, nested primers, and PROMOTERFINDER™ libraries to walk in genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length cDNA. Genomic libraries may be useful for extension of sequence into the 5' and 3' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled device camera. Output/light intensity may be converted to electrical signal using appropriate software (e.g. GENOTYPER™ and SEQUENCE NAVIGATOR™, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode MLF3, or fusion proteins or functional equivalents thereof, may be used in recombinant DNA molecules to direct expression of MLF3 in appropriate host cells. Due to the inherent degeneracy of the genetic code, other DNA sequences which encode substantially the same or a functionally equivalent amino acid sequence may be produced and these sequences may be used to clone and express MLF3.

As will be understood by those of skill in the art, it may be advantageous to produce MLF3-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

The nucleotide sequences of the present invention can be engineered using methods generally known in the art in order to alter MLF3 encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, or introduce mutations, and so forth.

In another embodiment of the invention, natural, modified, or recombinant nucleic acid sequences encoding MLF3 may be ligated to a heterologous sequence to encode a fusion protein. For example, to screen peptide libraries for inhibitors of MLF3 activity, it may be useful to encode a chimeric MLF3 protein that can be recognized by a commercially available antibody. A fusion protein may also be engineered to contain a cleavage site located between the MLF3 encoding sequence and the heterologous protein sequence, so that MLF3 may be cleaved and purified away from the heterologous moiety.

In another embodiment, sequences encoding MLF3 may be synthesized, in whole or in part, using chemical methods well known in the art (see Caruthers, M. H. et al. (1980) Nucl. Acids Res. Symp. Ser. 215–223, Horn, T. et al. (1980) Nucl. Acids Res. Symp. Ser. 225–232). Alternatively, the protein itself may be produced using chemical methods to synthesize the amino acid sequence of MLF3, or a portion thereof. For example, peptide synthesis can be performed using various solid-phase techniques (Roberge, J. Y. et al. (1995) Science 269:202–204) and automated synthesis may be achieved, for example, using the ABI 431A Peptide Synthesizer (Perkin Elmer).

The newly synthesized peptide may be substantially purified by preparative high performance liquid chromatography (e.g., Creighton, T. (1983) *Proteins, Structures and Molecular Principles,* W H Freeman and Co., New York, N.Y.). The composition of the synthetic peptides may be confirmed by amino acid analysis or sequencing (e.g., the Edman degradation procedure; Creighton, supra). Additionally, the amino acid sequence of MLF3, or any part thereof, may be altered during direct synthesis and/or combined using chemical methods with sequences from other proteins, or any part thereof, to produce a variant polypeptide.

In order to express a biologically active MLF3, the nucleotide sequences encoding MLF3 or functional equivalents, may be inserted into appropriate expression vector, i.e., a vector which contains the necessary elements for the transcription and translation of the inserted coding sequence.

Methods which are well known to those skilled in the art may be used to construct expression vectors containing sequences encoding MLF3 and appropriate transcriptional and translational control elements. These methods include in vitro recombinant DNA techniques, synthetic techniques, and in vivo genetic recombination. Such techniques are described in Sambrook, J. et al. (1989) *Molecular Cloning, A Laboratory Manual,* Cold Spring Harbor Press, Plainview, N.Y., and Ausubel, F. M. et al. (1989) *Current Protocols in Molecular Biology,* John Wiley & Sons, New York, N.Y.

A variety of expression vector/host systems may be utilized to contain and express sequences encoding MLF3. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT® phagemid (Stratagene, LaJolla, Calif.) or PSPORT™ plasmid (Gibco BRL) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding MLF3, vectors based on SV40 or EBV may be used with an appropriate selectable marker.

In bacterial systems, a number of expression vectors may be selected depending upon the use intended for MLF3. For example, when large quantities of MLF3 are needed for the induction of antibodies, vectors which direct high level expression of fusion proteins that are readily purified may be used. Such vectors include, but are not limited to, the multifunctional *E. coli* cloning and expression vectors such as BLUESCRIPT® (Stratagene), in which the sequence encoding MLF3 may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae,* a number of vectors containing constitutive or inducible promoters such as alpha factor, alcohol oxidase, and PGH may be used. For reviews, see Ausubel et al. (supra) and Grant et al. (1987) Methods Enzymol. 153:516–544. In cases where plant expression vectors are used, the expression of sequences encoding MLF3 may be driven by any of a number of promoters. For example, viral promoters such as the 35S and 19S promoters of CaMV may be used alone or in combination with the omega leader sequence from TMV (Takamatsu, N. (1987) EMBO J. 6:307–311). Alternatively, plant promoters such as the small subunit of RUBISCO or heat shock promoters may be used (Coruzzi, G. et al. (1984) EMBO J. 3:1671–1680; Broglie, R. et al. (1984) Science 224:838–843; and Winter, J. et al. (1991) Results Probl. Cell Differ. 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill *Yearbook of Science and Technology* (1992) McGraw Hill, New York, N.Y.; pp. 191–196).

An insect system may also be used to express MLF3. For example, in one such system, *Autographa californica* nuclear polyhedrosis virus (AcNPV) is used as a vector to express foreign genes in *Spodoptera frugiperda* cells or in Trichoplusia larvae. The sequences encoding MLF3 may be cloned into a non-essential region of the virus, such as the polyhedrin gene, and placed under control of the polyhedrin promoter. Successful insertion of MLF3 will render the polyhedrin gene inactive and produce recombinant virus lacking coat protein. The recombinant viruses may then be used to infect, for example, *S. frugiperda* cells or Trichoplusia larvae in which MLF3 may be expressed (Engelhard, E. K. et al. (1994) Proc. Natl. Acad. Sci. 91:3224–3227).

In mammalian host cells, a number of viral-based expression systems may be utilized. In cases where an adenovirus is used as an expression vector, sequences encoding MLF3 may be ligated into an adenovirus transcription/translation complex consisting of the late promoter and tripartite leader sequence. Insertion in a non-essential E1 or E3 region of the viral genome may be used to obtain a viable virus which is capable of expressing MLF3 in infected host cells (Logan, J. and Shenk, T. (1984) Proc. Natl. Acad. Sci. 81:3655–3659). In addition, transcription enhancers, such as the Rous sarcoma virus (RSV) enhancer, may be used to increase expression in mammalian host cells.

Specific initiation signals may also be used to achieve more efficient translation of sequences encoding MLF3. Such signals include the ATG initiation codon and adjacent sequences. In cases where sequences encoding MLF3, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells such as CHO (ATCC CCL 61 and CRL 9618), HeLa (ATCC CCL 2), MDCK (ATCC CCL 34 and CRL 6253), HEK 293 (ATCC CRL 1573), WI-38 (ATCC CCL 75) (ATCC: American Type Culture Collection, Rockville, Md.), which have specific cellular machinery and characteristic mechanisms for such post-translational activities, may be chosen to ensure the correct modification and processing of the foreign protein.

For long-term, high-yield production of recombinant proteins, stable expression is preferred. For example, cell lines which stably express MLF3 may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223–32) and adenine phosphoribosyltransferase (Lowy, I. et al. (1980) Cell 22:817–23) genes which can be employed in tk⁻ or aprt⁻ cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77:3567–70); npt, which confers resistance to the aminoglycosides neomycin and G-418 (Colbere- Garapin, F. et al (1981) J. Mol. Biol. 150:1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047–51). Recently, the use of visible markers has gained popularity with such markers as anthocyanins, β glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121–131).

Although the presence/absence of marker gene expression suggests that the gene of interest is also present, its presence and expression may need to be confirmed. For example, if the sequence encoding MLF3 is inserted within a marker gene sequence, recombinant cells containing sequences encoding MLF3 can be identified by the absence of marker gene function. Alternatively, a marker gene can be placed in tandem with a sequence encoding MLF3 under the control of a single promoter. Expression of the marker gene in response to induction or selection usually indicates expression of the tandem gene as well.

Alternatively, host cells which contain the nucleic acid sequence encoding MLF3 and express MLF3 may be identified by a variety of procedures known to those of skill in the art. These procedures include, but are not limited to, DNA—DNA or DNA-RNA hybridizations and protein bioassay or immunoassay techniques which include membrane, solution, or chip based technologies for the detection and/or quantification of nucleic acid or protein.

The presence of polynucleotide sequences encoding MLF3 can be detected by DNA—DNA or DNA-RNA hybridization or amplification using probes or portions or fragments of polynucleotides encoding MLF3. Nucleic acid amplification based assays involve the use of oligonucleotides or oligomers based on the sequences encoding MLF3 to detect transformants containing DNA or RNA encoding MLF3. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides, which can be used as a probe or amplimer.

A variety of protocols for detecting and measuring the expression of MLF3, using either polyclonal or monoclonal antibodies specific for the protein are known in the art. Examples include enzyme-linked immunosorbant assay (ELISA), radioimmunoassay (RIA), and fluorescence activated cell sorting (FACS). A two-site, monoclonal-based immunoassay utilizing monoclonal antibodies reactive to two non-interfering epitopes on MLF3 is preferred, but a competitive binding assay may be employed. These and other assays are described, among other places, in Hampton, R. et al. (1990; *Serological Methods, a Laboratory Manual*, APS Press, St Paul, Minn.) and Maddox, D. E. et al. (1983; J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding MLF3 include oligolabeling, nick translation, end-labeling or PCR amplification using a labeled nucleotide. Alternatively, the sequences encoding MLF3, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia & Upjohn, (Kalamazoo, Mich.); Promega (Madison Wis.); and U.S. Biochemical Corp., Cleveland, Ohio). Suitable reporter molecules or labels, which may be used, include radionuclides, enzymes, fluorescent, chemiluminescent, or chromogenic agents as well as substrates, cofactors, inhibitors, magnetic particles, and the like.

Host cells transformed with nucleotide sequences encoding MLF3 may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides which encode MLF3 may be designed to contain signal sequences which direct secretion of MLF3 through a prokaryotic or eukaryotic cell membrane.

Other recombinant constructions may be used to join sequences encoding MLF3 to nucleotide sequences encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and MLF3 may be used to facilitate purification. One such expression vector provides for expression of a fusion protein containing MLF3 and a nucleic acid encoding 6 histidine residues preceding a thioredoxin or an enterokinase cleavage site. The histidine residues facilitate purification on IMIAC (immobilized metal ion affinity chromatography) as described in Porath, J. et al. (1992, Prot. Exp. Purif. 3: 263–281) while the enterokinase cleavage site provides a means for purifying MLF3 from the fusion protein. A discussion of vectors which contain fusion proteins is provided in Kroll, D. J. et al. (1993; DNA Cell Biol. 12:441–453).

In addition to recombinant production, fragments of MLF3 may be produced by direct peptide synthesis using solid-phase techniques (Merrifield J. (1963) J. Am. Chem. Soc. 85:2149–2154). Protein synthesis may be performed using manual techniques or by automation. Automated synthesis may be achieved, for example, using Applied Biosystems 431A Peptide Synthesizer (Perkin Elmer). Various fragments of MLF3 may be chemically synthesized separately and combined using chemical methods to produce the full length molecule.

Therapeutics

Based on the chemical and structural homology among MLF3 (SEQ ID NO:1) and the human MLF1 and MLF2 proteins (SEQ ID NOS:3 and 5), MLF3 is a member of the MLF gene family. The rearrangement of the MLF1 gene [the t(3;5)(q25.1;q34) translocation] is associated with myelodysplastic syndrome and AML. The MLF2 gene maps to the short arm of human chromosome 12 which is frequently rearranged (translocations and deletions) in a broad spectrum of hematopoietic malignancies, including ALL, AML and myelodysplastic syndrome (Kuefer, M. U. et al., supra). Thus, chromosomal rearrangement of members of the MLF gene family are associated with hematopoietic malignancies and therefore the MLF3 gene provides a means to identify chromosomal rearrangements associated with hematopoietic malignancies. MLF3 is shown herein to be expressed in variety of tumors, particularly in breast, brain, stomach and paraganglionic tumors (FIGS. 4A and 4B). Furthermore, since the sequences encoding MLF3 were cloned from brain tumor tissue, MLF3 expression appears to be indicative of a proliferative state.

Therefore, in one embodiment, MLF3 or a fragment or derivative thereof may be administered to a subject to treat disorders associated with abnormal expression of MLF3, including a variety of tumors. Such conditions and diseases may include, but are not limited to, breast, brain, stomach and paraganglionic tumors.

In another embodiment, a vector capable of expressing MLF3, or a fragment or a derivative thereof, may also be administered to a subject to treat the breast, brain, stomach and paraganglionic tumors described above.

In another embodiment, MLF3 may be administered in combination with other conventional chemotherapeutic agents. The combination of therapeutic agents having different mechanisms of action will have synergistic effects allowing for the use of lower effective doses of each agent and lessening side effects.

In one aspect, antibodies which are specific for MLF3 may be used directly as an agonist, or indirectly as a targeting or delivery mechanism for bringing a pharmaceutical agent to cells or tissue which express MLF3.

In one embodiment, antagonists or inhibitors of MLF3 may be administered to a subject to treat or prevent tumors, particularly breast, brain, stomach and paraganglionic tumors.

In another embodiment, a vector expressing antisense of the polynucleotide encoding MLF3 may be administered to a subject to treat or prevent tumors, particularly breast, brain, stomach and paraganglionic tumors.

Antagonists or inhibitors of MLF3 may be produced using methods which are generally known in the art. In particular, purified MLF3 may be used to produce antibodies or to screen libraries of pharmaceutical agents to identify those which specifically bind MLF3.

Antibodies which are specific for MLF3 may be used directly as an antagonist, or indirectly as a targeting or delivery mechanism for bringing a pharmaceutical agent to cells or tissue which express MLF3. The antibodies may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which reduce or abolish MLF3 activity) are especially preferred for therapeutic use.

For the production of antibodies, various hosts including goats, rabbits, rats, mice, humans, and others, may be immunized by injection with MLF3 or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the peptides, fragments, or oligopeptides used to induce antibodies to MLF3 have an amino acid sequence consisting of at least five amino acids, and more preferably at least 10 amino acids. It is also preferable that they are identical to a portion of the amino acid sequence of the natural protein, and they may contain the entire amino acid sequence of a small, naturally occurring molecule. Short stretches of MLF3 amino acids may be fused with those of another protein such as keyhole limpet hemocyanin and antibody produced against the chimeric molecule.

Monoclonal antibodies to MLF3 may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; Cole, S. P. et al. (1984) Mol. Cell Biol. 62:109–120).

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81:6851–6855; Neuberger, M. S. et al. (1984) Nature 312:604–608; Takeda, S. et al. (1985) Nature 314:452–454). Alternatively, techniques described for the production of single chain antibodies may be adapted, using methods known in the art, to produce MLF3-specific single chain antibodies. Antibodies with related specificity, but of distinct idiotypic composition, may be generated by chain shuffling from random combinatorial immunoglobin libraries (Burton D. R. (1991) Proc. Natl. Acad. Sci. 88:11120–3).

Antibodies may also be produced by inducing in vivo production in the lymphocyte population or by screening recombinant immunoglobulin libraries or panels of highly specific binding reagents as disclosed in the literature (Orlandi, R. et al. (1989) Proc. Natl. Acad. Sci. 86: 3833–3837; Winter, G. et al. (1991) Nature 349:293–299).

Antibody fragments which contain specific binding sites for MLF3 may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse, W. D. et al. (1989) Science 254:1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between MLF3 and its specific antibody. A two-site, monoclonal-based immunoassay utilizing monoclonal antibodies reactive to two non-interfering MLF3 epitopes is preferred, but a competitive binding assay may also be employed (Maddox, supra).

In another embodiment of the invention, the polynucleotides encoding MLF3, or any fragment thereof, or antisense molecules, may be used for therapeutic purposes. In one aspect, antisense to the polynucleotide encoding MLF3 may be used in situations in which it would be desirable to block the transcription of the mRNA. In particular, cells may be transformed with sequences complementary to polynucleotides encoding MLF3. Thus, antisense molecules may be used to modulate MLF3 activity, or to achieve regulation of gene function. Such technology is now well known in the art, and sense or antisense oligomers or larger fragments, can be designed from various locations along the coding or control regions of sequences encoding MLF3.

Expression vectors derived from retroviruses, adenovirus, herpes or vaccinia viruses, or from various bacterial plasmids may be used for delivery of nucleotide sequences to the targeted organ, tissue or cell population. Methods which are well known to those skilled in the art can be used to construct recombinant vectors which will express antisense molecules complementary to the polynucleotides of the gene encoding MLF3. These techniques are described both in Sambrook et al. (supra) and in Ausubel et al. (supra).

Genes encoding MLF3 can be turned off by transforming a cell or tissue with expression vectors which express high levels of a polynucleotide or fragment thereof which encodes MLF3. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing antisense molecules, DNA, RNA, or PNA, to the control regions of the gene encoding MLF3, i.e., the promoters, enhancers, and introns. Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches,* Futura Publishing Co., Mt. Kisco, N.Y.). The antisense molecules may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding MLF3.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding MLF3. Such DNA sequences may be incorporated into a wide variety of vectors with suitable RNA polymerase promoters such as T7 or SP6. Alternatively, these cDNA constructs that synthesize antisense RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection and by liposome injections may be achieved using methods which are well known in the art.

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of MLF3, antibodies to MLF3, mimetics, agonists, antagonists, or inhibitors of MLF3. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of MLF3, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example MLF3 or fragments thereof, antibodies of MLF3, agonists, antagonists or inhibitors of MLF3, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50.

Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind MLF3 may be used for the diagnosis of conditions or diseases characterized by expression of MLF3, or in assays to monitor patients being treated with MLF3, agonists, antagonists or inhibitors. The antibodies useful for diagnostic purposes may be prepared in the same manner as those described above for therapeutics. Diagnostic assays for MLF3 include methods which utilize the antibody and a label to detect MLF3 in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring MLF3 are known in the art and provide a basis for diagnosing altered or abnormal levels of MLF3 expression. Normal or standard values for MLF3 expression are established by combining body fluids or cell extracts taken from normal mammalian subjects, preferably human, with antibody to MLF3 under conditions suitable for complex formation. The amount of standard complex formation may be quantified by various methods, but preferably by photometric means. Quantities of MLF3 expressed in subject, control, and disease samples from biopsied tissues are compared with the standard values. Deviation between standard and subject values establishes the parameters for diagnosing disease.

In another embodiment of the invention, the polynucleotides encoding MLF3 are used for diagnostic purposes. The polynucleotides which may be used include oligonucleotide sequences, antisense RNA and DNA molecules, and PNAs. The polynucleotides may be used to detect and quantitate gene expression in biopsied tissues in which expression of MLF3 may be correlated with disease. The diagnostic assay may be used to distinguish between absence, presence, and excess expression of MLF3, and to monitor regulation of MLF3 levels during therapeutic intervention.

In one aspect, hybridization with PCR probes which are capable of detecting polynucleotide sequences, including genomic sequences, encoding MLF3 or closely related molecules, may be used to identify nucleic acid sequences which encode MLF3. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding MLF3, alleles, or related sequences.

Probes may also be used for the detection of related sequences, and should preferably contain at least 50% of the nucleotides from any of the MLF3 encoding sequences. The hybridization probes of the subject invention may be DNA or RNA and derived from the nucleotide sequence of SEQ ID NO:2 or from genomic sequence including promoter, enhancer elements, and introns of the naturally occurring MLF3.

Means for producing specific hybridization probes for DNAs encoding MLF3 include the cloning of nucleic acid sequences encoding MLF3 or MLF3 derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as $^{32}P$ or $^{35}S$, or enzymatic labels, such as alkaline phosphatase coupled to the probe via avidin/biotin coupling systems, and the like.

Polynucleotide sequences encoding MLF3 may be used for the diagnosis of conditions or diseases which are associated with expression of MLF3. Examples of such conditions or diseases include hematopoietic malignancies and, breast, brain, stomach and paraganglionic tumors. The polynucleotide sequences encoding MLF3 may be used in Southern or northern analysis, dot blot, or other membrane-based technologies; in PCR technologies; or in dip stick, pin, ELISA or chip assays utilizing fluids or tissues from patient biopsies to detect altered MLF3 expression. Such qualitative or quantitative methods are well known in the art.

In a particular aspect, the nucleotide sequences encoding MLF3 provide the basis for assays that detect activation or induction of various cancers, particularly those mentioned above; in addition the lack of expression of MLF3 may be detected using the MLF3-encoding nucleotide sequences disclosed herein. The nucleotide sequences encoding MLF3 may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding MLF3 in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of MLF3, a normal or standard profile for expression is established. This may be accomplished by combining body fluids or cell extracts taken from normal subjects, either animal or human, with a sequence, or a fragment thereof, which encodes MLF3, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively low or a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding MLF3 may involve the use of PCR. Such oligomers may be chemically synthesized, generated enzymatically, or produced from a recombinant source. Oligomers will preferably consist of two nucleotide sequences, one with sense orientation (5→3') and another with antisense (3'←5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of MLF3 include radiolabeling or biotinylating nucleotides, coamplification of a control nucleic acid, and standard curves onto which the experimental results are interpolated (Melby, P. C. et al. (1993) J. Immunol. Methods, 159:235–244; Duplaa, C. et al. (1993) Anal. Biochem. 229–236). The speed of quantitation of multiple samples may be accelerated by running the assay in an ELISA format where the oligomer of interest is presented in various dilutions and a spectrophotometric or colorimetric response gives rapid quantitation.

In another embodiment of the invention, the nucleic acid sequences which encode MLF3 may also be used to generate hybridization probes which are useful for mapping the naturally occurring genomic sequence. The sequences may be mapped to a particular chromosome or to a specific region of the chromosome using well known techniques. Such techniques include FISH, FACS, or artificial chromosome constructions, such as yeast artificial chromosomes, bacterial artificial chromosomes, bacterial P1 constructions or single chromosome cDNA libraries as reviewed in Price, C. M. (1993) Blood Rev. 7:127–134, and Trask, B. J. (1991) Trends Genet. 7:149–154.

FISH (as described in Verma et al. (1988) *Human Chromosomes: A Manual of Basic Techniques,* Pergamon Press, New York, N.Y.) may be correlated with other physical chromosome mapping techniques and genetic map data. Examples of genetic map data can be found in the 1994 Genome Issue of Science (265: 1981f). Correlation between the location of the gene encoding MLF3 on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22-23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals, particularly translocations and deletions associated with hematopoietic malignancies (e.g., AML and myelodysplastic syndrome).

In another embodiment of the invention, MLF3, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between MLF3 and the agent being tested, may be measured.

Another technique for drug screening which may be used provides for high throughput screening of compounds having suitable binding affinity to the protein of interest as described in published PCT application WO84/03564. In this method, as applied to MLF3 large numbers of different small test compounds are synthesized on a solid substrate, such as plastic pins or some other surface. The test compounds are reacted with MLF3, or fragments thereof, and washed. Bound MLF3 is then detected by methods well known in the art. Purified MLF3 can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding MLF3 specifically compete with a test compound for binding MLF3. In this manner, the antibodies can be used to detect the presence of any peptide which shares one or more antigenic determinants with MLF3.

In additional embodiments, the nucleotide sequences which encode MLF3 may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I BRAITUT02 cDNA Library Construction

The BRAITUT02 cDNA library was constructed using 1 microgram of polyA RNA isolated from brain tumor tissue removed from the frontal lobe of a 58-year-old Caucasian male during excision of a cerebral meningeal lesion. Pathology indicated a grade 2 metastatic hypernephroma. The patient presented with migraine headache, developed a cerebral hemorrhage and pulmonary edema, and died during hospitalization. Patient history included a grade 2 renal cell carcinoma, insomnia, and chronic airway obstruction. Previous surgeries included a nephroureterectomy. Patient medications included Decadron (dexamethasone) and Dilantin (phenytoin).

The frozen tissue was homogenized and lysed using a Brinkmann Homogenizer Polytron PT-3000 (Brinkmann Instruments, Westbury N.J.). The lysate was centrifuged over a 5.7M CsCl cushion using a Beckman SW28 rotor in a Beckman L8-70M Ultracentrifuge (Beckman Instruments) for 18 hours at 25,000 rpm at ambient temperature. The RNA was extracted with phenol chloroform pH 4.0, precipitated using 0.3M sodium acetate and 2.5 volumes of ethanol, resuspended in RNAse-free water and DNase treated at 37° C. Extraction and precipitation were repeated as above. RNA was isolated with the QIAGEN OLIGOTEX kit (QIAGEN Inc; Chatsworth Calif.) and used to construct the cDNA library.

The RNA was handled according to the recommended protocols in the SuperScript Plasmid System for cDNA Synthesis and Plasmid Cloning (Cat. #18248-013; Gibco/BRL, Gaithersburg, Md.). cDNAs were fractionated on a Sepharose CL4B column (Cat. #275105, Pharmacia), and those cDNAs exceeding 400 bp were ligated into PSPORT1. The plasmid PSPORT1 was subsequently transformed into DH5α™ competent cells (Cat. #18258-012, Gibco/BRL).

II Isolation and Sequencing of cDNA Clones

Plasmid DNA was released from the cells and purified using the Miniprep Kit (Catalog #77468; Advanced Genetic Technologies Corporation, Gaithersburg Md.). This kit consists of a 96-well block with reagents for 960 purifications. The recommended protocol was employed except for the following changes: 1) the 96 wells were each filled with only 1 ml of sterile Terrific Broth (Catalog #22711, Gibco/BRL) with carbenicillin at 25 mg/L and glycerol at 0.4%; 2) the bacteria were cultured for 24 hours after the wells were inoculated and then lysed with 60 μl of lysis buffer; 3) a centrifugation step employing the Beckman GS-6R rotor at 2900 rpm for 5 minutes was performed before the contents of the block were added to the primary filter plate; and 4) the optional step of adding isopropanol to TRIS buffer was not routinely performed. After the last step in the protocol, samples were transferred to a Beckman 96-well block for storage.

The cDNAs were sequenced by the method of Sanger F and A R Coulson (1975; J Mol Biol 94:441f), using a Hamilton Micro Lab 2200 (Hamilton, Reno Nev.) in combination with four Peltier Thermal Cyclers (PTC200 from MJ Research, Watertown Mass.) and Applied Biosystems 377 or 373 DNA Sequencing Systems, and the reading frame was determined.

III Homology Searching of cDNA Clones and Their Deduced Proteins

Nucleotide or deduced amino acid sequences were used as query sequences against databases such as GenBank, SwissProt, BLOCKS, and Pima II. These databases which contain previously identified and annotated sequences were searched for regions of homology (similarity) using BLAST (Basic Local Alignment Search Tool; Altschul (1993) supra, Altschul (1990) supra).

BLAST produces alignments of both nucleotide and amino acid sequences to determine sequence similarity. Because of the local nature of the alignments, BLAST is especially useful in determining exact matches or in identifying homologs which may be of prokaryotic (bacterial) or eukaryotic (animal, fungal or plant) origin. Other algorithms such as the one described in Smith R F and T F Smith (1992 Protein Engineering 5:35–51), incorporated herein by reference, can be used when dealing with primary sequence patterns and secondary structure gap penalties. As disclosed in this application, the sequences have lengths of at least 49 nucleotides, and no more than 12% uncalled bases (where N is recorded rather than A, C, G, or T).

The BLAST approach, as detailed in Karlin and Altschul (supra) and incorporated herein by reference, searches matches between a query sequence and a database sequence, to evaluate the statistical significance of any matches found, and to report only those matches which satisfy the user-selected threshold of significance. In this application, threshold was set at $10^{-25}$ for nucleotides and $10^{-14}$ for peptides.

Incyte nucleotide sequences were searched against the GenBank databases for primate (pri), rodent (rod), and mammalian sequences (mam), and deduced amino acid sequences from the same clones are searched against GenBank functional protein databases, mammalian (mamp), vertebrate (vrtp) and eukaryote (eukp), for homology. The relevant database for a particular match were reported as a GIxxx±p (where xxx is pri, rod, etc. and if present, p=peptide).

A comparison of the full-length and partial cDNA sequences and the deduced amino acid sequences corresponding to the human MLF3 gene and MLF3 protein with known nucleotide and protein sequences in GenBank revealed that the full-length human MLF3 cDNA and protein sequences (i.e., SEQ ID NOS:1 and 2) were unique (i.e., not previously identified). This search revealed that the human MLF3 protein shared some homology with the human MLF1 protein (SEQ ID NO:3) and the human MLF2 protein (SEQ ID NO:5). In addition, portions of the amino acid sequence of MLF3 were found to share homology with a number of short EST sequences of human origin (GI 649669, GI 878231, GI 698722, GI 946359 and GI 876176). The five sequences producing the highest-scoring segment pairs from the GenBank search are shown below in Table 1. In Table 1, "EST" is an abbreviation for expressed sequence tag.; the column designations in Table 1 below are as described above.

TABLE 1

| Database | Accession No. | Score | P(N) | Release | Description |
|---|---|---|---|---|---|
| GIpri | g1399745 | 1232 | 3.6e − 166 | genpept97 | MLF2 |
| GIpri | g1066392 | 354 | 9.6e − 50 | genpept97 | MLF1 |
| GIpri | g649669 | 321 | 3.0e − 54 | gb97merck | EST |
| GIpri | g878231 | 312 | 3.7e − 37 | gb97merck | EST |
| GIpri | g698722 | 267 | 2.7e − 30 | gb97merck | EST |

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques using BLAST (Altschul, S. F. 1993 and 1990, supra) are used to search for identical or related molecules in nucleotide databases such as GenBank or the LIFESEQ™ database (Incyte Pharmaceuticals). This analysis is much faster than multiple, membrane-based hybridizations. In addition, the sensitivity of the computer search can be modified to determine whether any particular match is categorized as exact or homologous.

The basis of the search is the product score which is defined as:

$$\% \text{ sequence identity} \times \% \text{ maximum BLAST score}/100$$

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding MLF3 occurs. Abundance and percent abundance are also reported. Abundance directly reflects the number of times a particular transcript is represented in a cDNA library, and percent abundance is abundance divided by the total number of sequences examined in the cDNA library.

Electronic northern analysis (FIGS. 4A and 4B) revealed that mRNA encoding human MLF3 (SEQ ID NO:1) was present in libraries generated from a variety of adult and fetal tissues. MLF3 cDNA is most strongly expressed in the brain; at least 15% of the libraries containing MLF3 sequences were derived from either normal or diseased brain tissue. In addition to expression in apparently normal human tissues, MLF3 was expressed in a variety of tumors, including but not limited to breast, brain, stomach, and paraganglionic tumors as well as in an immortalized cell line (the hNT2 teratocarcinoma cell line). MLF3 cDNA was also expressed in a variety of tissues and cell lines which are in the hematopoietic lineages and/or involved with the immune response, including bone marrow, spleen, lymph node, macrophages, and tissues associated with inflammatory and/or autoimmune disease (e.g., Crohn's disease).

V Extension of MLF3-Encoding Polynucleotides

The nucleic acid sequence (SEQ ID NO:2) encoding MLF3 is used to design oligonucleotide primers for extending a partial nucleotide sequence to full length or for obtaining 5' or 3', intron or other control sequences from genomic libraries. One primer is synthesized to initiate extension in the antisense direction (XLR) and the other is synthesized to extend sequence in the sense direction (XLF). Primers are used to facilitate the extension of the known sequence "outward" generating amplicons containing new, unknown nucleotide sequence for the region of interest. The initial primers are designed from the cDNA using OLIGO 4.06 (National Biosciences), or another appropriate program, to be 22–30 nucleotides in length, to have a GC content of 50% or more, and to anneal to the target sequence at temperatures about 68°–72° C. Any stretch of nucleotides which would result in hairpin structures and primer—primer dimerizations is avoided.

The original, selected cDNA libraries, or a human genomic library are used to extend the sequence; the latter is most useful to obtain 5' upstream regions. If more extension is necessary or desired, additional sets of primers are designed to further extend the known region.

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier Thermal Cycler (PTC200; M.J. Research, Watertown, Mass.) and the following parameters:

Step 1 94° C. for 1 min (initial denaturation)
Step 2 65° C. for 1 min
Step 3 68° C. for 6 min
Step 4 94° C. for 15 sec
Step 5 65° C. for 1 min
Step 6 68° C. for 7 min
Step 7 Repeat step 4–6 for 15 additional cycles
Step 8 94° C. for 15 sec
Step 9 65° C. for 1 min
Step 10 68° C. for 7:15 min
Step 11 Repeat step 8–10 for 12 cycles
Step 12 72° C. for 8 min
Step 13 4° C. (and holding)

A 5–10 μl aliquot of the reaction mixture is analyzed by electrophoresis on a low concentration (about 0.6–0.8%) agarose mini-gel to determine which reactions were successful in extending the sequence. Bands thought to contain the largest products are selected and removed from the gel. Further purification involves using a commercial gel extraction method such as QIAQUICK™ (QIAGEN Inc., Chatsworth, Calif.). After recovery of the DNA, Klenow enzyme is used to trim single-stranded, nucleotide overhangs creating blunt ends which facilitate religation and cloning.

After ethanol precipitation, the products are redissolved in 13 μl of ligation buffer, 1 μl T4-DNA ligase (15 units) and 1 μl T4 polynucleotide kinase are added, and the mixture is incubated at room temperature for 2–3 hours or overnight at 16° C. Competent E. coli cells (in 40 μl of appropriate media) are transformed with 3 μl of ligation mixture and cultured in 80 μl of SOC medium (Sambrook et al., supra). After incubation for one hour at 37° C., the whole transformation mixture is plated on Luria Bertani (LB)-agar (Sambrook et al., supra) containing 2× Carb. The following day, several colonies are randomly picked from each plate and cultured in 150 μl of liquid LB/2× Carb medium placed in an individual well of an appropriate, commercially-available, sterile 96-well microtiter plate. The following day, 5 μl of each overnight culture is transferred into a non-sterile 96-well plate and after dilution 1:10 with water, 5 μl of each sample is transferred into a PCR array.

For PCR amplification, 18 μl of concentrated PCR reaction mix (3.3×) containing 4 units of rTth DNA polymerase, a vector primer, and one or both of the gene specific primers used for the extension reaction are added to each well. Amplification is performed using the following conditions:

Step 1 94° C. for 60 sec
Step 2 94° C. for 20 sec
Step 3 55° C. for 30 sec
Step 4 72° C. for 90 sec
Step 5 Repeat steps 2–4 for an additional 29 cycles
Step 6 72° C. for 180 sec
Step 7 4° C. (and holding)

Aliquots of the PCR reactions are run on agarose gels together with molecular weight markers. The sizes of the PCR products are compared to the original partial cDNAs, and appropriate clones are selected, ligated into plasmid, and sequenced.

VI Labeling and Use of Hybridization Probes

Hybridization probes derived from SEQ ID NO:2 are employed to screen cDNAs, genomic DNAs, or mRNAs. Although the labeling of oligonucleotides, consisting of about 20 base-pairs, is specifically described, essentially the same procedure is used with larger cDNA fragments. Oligonucleotides are designed using state-of-the-art software such as OLIGO 4.06 (National Biosciences), labeled by combining 50 pmol of each oligomer and 250 μCi of [γ-$^{32}$P] adenosine triphosphate (Amersham) and T4 polynucleotide kinase (DuPont NEN®, Boston, Mass.). The labeled oligonucleotides are substantially purified with Sephadex G-25 superfine resin column (Pharmacia & Upjohn). A portion containing $10^7$ counts per minute of each of the sense and antisense oligonucleotides is used in a typical membrane based hybridization analysis of human genomic DNA digested with one of the following endonucleases (Ase I, Bgl II, Eco RI, Pst I, Xba 1, or Pvu II; DuPont NEN®).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT AR™ film (Kodak, Rochester, N.Y.) is exposed to the blots in a Phosphoimager cassette (Molecular Dynamics, Sunnyvale, Calif.) for several hours, hybridization patterns are compared visually.

VII Antisense Molecules

Antisense molecules to the MLF3-encoding sequence, or any part thereof, is used to inhibit in vivo or in vitro expression of naturally occurring MLF3. Although use of antisense oligonucleotides, comprising about 20 base-pairs, is specifically described, essentially the same procedure is used with larger cDNA fragments. An oligonucleotide based on the coding sequences of MLF3, as shown in FIGS. 1A and 1B, is used to inhibit expression of naturally occurring MLF3. The complementary oligonucleotide is designed from the most unique 5' sequence as shown in FIGS. 1A and 1B and used either to inhibit transcription by preventing promoter binding to the upstream nontranslated sequence or translation of an MLF3-encoding transcript by preventing the ribosome from binding. Using an appropriate portion of the signal and 5' sequence of SEQ ID NO:2, an effective antisense oligonucleotide includes any 15–20 nucleotides spanning the region which translates into the signal or 5' coding sequence of the polypeptide as shown in FIGS. 1A and 1B.

VIII Expression of MLF3

Expression of MLF3 is accomplished by subcloning the cDNAs into appropriate vectors and transforming the vectors into host cells. In this case, the cloning vector, PSPORT, previously used for the generation of the cDNA library is used to express MLF3 in E. coli. Upstream of the cloning site, this vector contains a promoter for β-galactosidase, followed by sequence containing the amino-terminal Met, and the subsequent seven residues of β-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of β-galactosidase, about 5 to residues of linker, and the full length protein or fragments thereof. The signal residues present on the pSport vector direct the secretion of MLF3 into the bacterial growth media.

IX Demonstration of MLF3 Activity

Given the chemical and structural similarity between the human MLF3 protein and human MLF1 and MLF2 proteins, MLF3 is presumed to be a cytoplasmic protein. To demonstrate that MLF3 is a cytoplasmic protein, sequences encoding MLF3 are expressed in cells which lack the ability to express MLF3 and the location of MLF3 is ascertained using conventional techniques (e.g., immunoprecipitation of proteins derived from cell membrane-containing fractions and soluble fractions lacking membrane-associated proteins; preparation of anti-MLF3 antibodies is described below). Expression of MLF3 is achieved using methods known to the art as described above; numerous expression vectors are available for the expression of proteins in eukaryotic and prokaryotic hosts.

Cells which lack the ability to express human MLF3 are easily obtained as any non-human human eukaryotic cell line is expected to lack the ability to express human MLF3; in addition, prokaryotic cells would lack the ability to express MLF3. Confirmation that a cell lacks the ability to express MLF3 is obtained by a variety of means known to the art including Northern blot analysis in which RNA isolated from the candidate host cell is hybridized with MLF3-encoding sequences (e.g., SEQ ID NO:2); cells whose RNA fails to hybridize with MLF3 sequences are suitable MLF3-negative host cells. In addition, anti-MLF3 antibodies can be used to confirm that the candidate host cell lacks proteins which react or cross-react with MLF3.

The monkey cell line COS-7 (ATCC CRL 1651) is particularly preferred when used in conjunction with an expression vector containing the SV40 origin of replication (SV40 ori) and MLF3 sequences for determining the cellular localization of the MLF3 protein. An SV40 ori-containing MLF3 expression vector is transferred (e.g., electroporated) into COS-7 cells and the transiently overexpressed MLF3 protein is localized using standard immunohistochemical or immunofluorescence techniques on fixed an permeabilized transformed COS-7 cells.

X Production of MLF3 Specific Antibodies

MLF3 that is substantially purified using PAGE electrophoresis (Sambrook, supra), or other purification techniques, is used to immunize rabbits and to produce antibodies using standard protocols. The amino acid sequence deduced from SEQ ID NO:2 is analyzed using DNASTAR software (DNASTAR Inc) to determine regions of high immunogenicity and a corresponding oligopolypeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems Peptide Synthesizer Model 431A using fmoc-chemistry, and coupled to keyhole limpet hemocyanin (KLH, Sigma, St. Louis, Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

XI Purification of Naturally Occurring MLF3 Using Specific Antibodies

Naturally occurring or recombinant MLF3 is substantially purified by immunoaffinity chromatography using antibodies specific for MLF3. An immunoaffinity column is constructed by covalently coupling MLF3 antibody to an activated chromatographic resin, such as CnBr-activated Sepharose (Pharmacia & Upjohn). After the coupling, the resin is blocked and washed according to the manufacturer's instructions.

Media containing MLF3 is passed over the immunoaffinity column, and the column is washed under conditions that allow the preferential absorbance of MLF3 (e.g., high ionic strength buffers in the presence of detergent). The column is eluted under conditions that disrupt antibody/MLF3 binding (eg, a buffer of pH 2–3 or a high concentration of a chaotrope, such as urea or thiocyanate ion), and MLF3 is collected.

XII Identification of Molecules Which Interact with MLF3

MLF3 or biologically active fragments thereof are labeled with $^{125}$I Bolton-Hunter reagent (Bolton et al. (1973) Biochem. J. 133: 529). Candidate molecules previously arrayed in the wells of a multi-well plate are incubated with the labeled MLF3, washed and any wells with labeled MLF3 complex are assayed. Data obtained using different concentrations of MLF3 are used to calculate values for the number, affinity, and association of MLF3 with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. An isolated and purified polynucleotide sequence encoding the polypeptide comprising the amino acid sequence of SEQ ID NO:1.

2. A polynucleotide sequence which is fully complementary to the polynucleotide sequence of claim 1.

3. An isolated and purified polynucleotide sequence comprising SEQ ID NO:2.

4. An isolated and purified polynucleotide sequence which is complementary to SEQ ID NO:2.

5. An expression vector containing the polynucleotide sequence of claim 1.

6. A host cell containing the vector of claim 5.

7. A method for producing a polypeptide comprising the amino acid sequence of SEQ ID NO:1 or fragments thereof, the method comprising the steps of:

a) culturing the host cell of claim 6 under conditions suitable for the expression of the polypeptide; and b) recovering the polypeptide from the host cell culture.

8. A method for detection of polynucleotides encoding the amino acid sequence of SEQ ID NO:1 in a biological sample containing nucleic acid material, the method comprising the steps of:

a) hybridizing the polynucleotide of claim 6 to the nucleic acid material of the biological sample, thereby forming a hybridization complex;

b) washing the hybridization complex under conditions of at least 0.1× saline sodium citrate and 0.5% sodium dodecyl sulfate; and c) detecting the hybridization complex, wherein the presence of the hybridization complex correlates with the presence of a polynucleotide encoding the amino acid sequence of SEQ ID NO:1 in the biological sample.

9. The method of claim 8, wherein before the hybridizing step, the nucleic acid material of the biological sample is amplified by the polymerase chain reaction.

\* \* \* \* \*

UNITED STATES PATENT AND TRADEMARK OFFICE
CERTIFICATE OF CORRECTION

PATENT NO. : 5,851,774
DATED : December 22, 1998
INVENTOR(S) : Hillman et al.

It is certified that error appears in the above-identified patent and that said Letters Patent is hereby corrected as shown below:

Column 46,
Line 5, delete "claim 6" and insert -- claim 4 --.

Signed and Sealed this

Fourth Day of February, 2003

JAMES E. ROGAN
*Director of the United States Patent and Trademark Office*